(12) United States Patent
Bai et al.

(10) Patent No.: US 11,324,471 B2
(45) Date of Patent: May 10, 2022

(54) ASYMMETRIC SCATTER FITTING FOR OPTIMAL PANEL READOUT IN CONE-BEAM COMPUTED TOMOGRAPHY

(71) Applicant: Accuray, Inc., Sunnyvale, CA (US)

(72) Inventors: Chuanyong Bai, Solon, OH (US); Amit Jain, Solon, OH (US); Daniel Gagnon, Twinsburg, OH (US); Zhicong Yu, Highland Hts., OH (US); Jacob Shea, Madison, WI (US)

(73) Assignee: Accuray Inc., Sunnyvale, CA (US)

( * ) Notice: Subject to any disclaimer, the term of this patent is extended or adjusted under 35 U.S.C. 154(b) by 64 days.

(21) Appl. No.: 16/694,210

(22) Filed: Nov. 25, 2019

(65) Prior Publication Data

US 2020/0170592 A1  Jun. 4, 2020

Related U.S. Application Data

(60) Provisional application No. 62/878,364, filed on Jul. 25, 2019, provisional application No. 62/843,796, (Continued)

(51) Int. Cl.
*A61B 6/00* (2006.01)
*G06T 11/00* (2006.01)
(Continued)

(52) U.S. Cl.
CPC ............ *A61B 6/5282* (2013.01); *A61B 6/027* (2013.01); *A61B 6/032* (2013.01); *A61B 6/06* (2013.01);
(Continued)

(58) Field of Classification Search
None
See application file for complete search history.

(56) References Cited

U.S. PATENT DOCUMENTS

| 4,190,773 A | 2/1980 | Braden et al. |
| 5,615,279 A | 3/1997 | Yoshioka et al. |

(Continued)

FOREIGN PATENT DOCUMENTS

| DE | 10 2006 007058 A1 | 7/2007 |
| EP | 1062914 A1 | 12/2000 |

(Continued)

OTHER PUBLICATIONS

Office Action from U.S. Appl. No. 16/694,145 dated Mar. 17, 2021, 10 pages.

(Continued)

*Primary Examiner* — Hoon K Song
(74) *Attorney, Agent, or Firm* — Calfee, Halter & Griswold LLP

(57) ABSTRACT

An x-ray imaging apparatus and associated methods are provided to receive measured projection data in a primary region and measured scatter data in asymmetrical shadow regions and determine an estimated scatter in the primary region based on the measured scatter data in the shadow region(s). The asymmetric shadow regions can be controlled by adjusting the position of the beam aperture center on the readout area of the detector. Penumbra data may also be used to estimate scatter in the primary region.

19 Claims, 16 Drawing Sheets

Related U.S. Application Data filed on May 6, 2019, provisional application No. 62/836,352, filed on Apr. 19, 2019, provisional application No. 62/836,357, filed on Apr. 19, 2019, provisional application No. 62/821,116, filed on Mar. 20, 2019, provisional application No. 62/813,335, filed on Mar. 4, 2019, provisional application No. 62/801,260, filed on Feb. 5, 2019, provisional application No. 62/800,287, filed on Feb. 1, 2019, provisional application No. 62/796,831, filed on Jan. 25, 2019, provisional application No. 62/773,700, filed on Nov. 30, 2018, provisional application No. 62/773,712, filed on Nov. 30, 2018.

(51) Int. Cl.
*A61B 6/03* (2006.01)
*A61B 6/06* (2006.01)
*A61B 6/02* (2006.01)
*A61N 5/10* (2006.01)
*A61B 6/08* (2006.01)
*G06T 7/30* (2017.01)
*A61B 5/055* (2006.01)
*A61B 6/04* (2006.01)

(52) U.S. Cl.
CPC ............ *A61B 6/405* (2013.01); *A61B 6/4078* (2013.01); *A61B 6/4085* (2013.01); *A61B 6/469* (2013.01); *A61B 6/488* (2013.01); *A61B 6/5205* (2013.01); *G06T 11/005* (2013.01); *A61B 5/055* (2013.01); *A61B 6/025* (2013.01); *A61B 6/03* (2013.01); *A61B 6/035* (2013.01); *A61B 6/0407* (2013.01); *A61B 6/08* (2013.01); *A61B 6/4014* (2013.01); *A61B 6/4021* (2013.01); *A61B 6/4028* (2013.01); *A61B 6/4064* (2013.01); *A61B 6/4435* (2013.01); *A61B 6/4441* (2013.01); *A61B 6/4458* (2013.01); *A61B 6/481* (2013.01); *A61B 6/482* (2013.01); *A61B 6/483* (2013.01); *A61B 6/484* (2013.01); *A61B 6/541* (2013.01); *A61B 6/582* (2013.01); *A61N 5/107* (2013.01); *A61N 5/1049* (2013.01); *A61N 5/1067* (2013.01); *A61N 5/1071* (2013.01); *A61N 5/1082* (2013.01); *A61N 2005/1085* (2013.01); *A61N 2005/1091* (2013.01); *A61N 2005/1095* (2013.01); *G06T 7/30* (2017.01); *G06T 11/008* (2013.01); *G06T 2207/10081* (2013.01); *G06T 2210/41* (2013.01); *G06T 2211/404* (2013.01); *G06T 2211/412* (2013.01); *G06T 2211/424* (2013.01); *G06T 2211/428* (2013.01); *G06T 2211/432* (2013.01)

(56) References Cited

U.S. PATENT DOCUMENTS

| | | |
|---|---|---|
| 6,233,478 B1 | 5/2001 | Liu |
| 6,307,909 B1 | 10/2001 | Flohr et al. |
| 7,050,528 B2 | 5/2006 | Chen |
| 7,336,759 B2 | 2/2008 | Nukui |
| 7,660,380 B2 | 2/2010 | Boese et al. |
| 8,116,430 B1 | 2/2012 | Shapiro et al. |
| 8,467,497 B2 | 6/2013 | Lu et al. |
| 8,588,363 B2 | 11/2013 | Flohr |
| 9,400,332 B2 | 7/2016 | Star-Lack et al. |
| 2003/0007601 A1 | 1/2003 | Jaffray et al. |
| 2003/0076927 A1 | 4/2003 | Shigeyuki et al. |
| 2004/0091079 A1 | 5/2004 | Zapalac |
| 2004/0202360 A1 | 10/2004 | Besson |
| 2005/0053188 A1 | 3/2005 | Gohno |
| 2005/0251029 A1 | 11/2005 | Khamene et al. |
| 2006/0109954 A1* | 5/2006 | Gohno ................ A61B 6/032 378/98.12 |
| 2006/0262894 A1 | 11/2006 | Bernhadt et al. |
| 2007/0127621 A1 | 6/2007 | Grass et al. |
| 2007/0189444 A1 | 8/2007 | Van Steven-Daal et al. |
| 2008/0103834 A1 | 5/2008 | Reiner |
| 2008/0112532 A1 | 5/2008 | Schlomka et al. |
| 2009/0080603 A1 | 3/2009 | Shukla et al. |
| 2009/0135994 A1 | 5/2009 | Yu et al. |
| 2009/0161826 A1 | 6/2009 | Gertner et al. |
| 2009/0225932 A1 | 9/2009 | Zhu et al. |
| 2009/0283682 A1 | 11/2009 | Star-Lack et al. |
| 2009/0304142 A1 | 12/2009 | Ruimi et al. |
| 2010/0046819 A1 | 2/2010 | Noo et al. |
| 2010/0142791 A1 | 6/2010 | Tsuji |
| 2010/0208964 A1 | 8/2010 | Wiegert et al. |
| 2011/0142312 A1 | 6/2011 | Toth et al. |
| 2011/0255656 A1 | 10/2011 | Star-Lack et al. |
| 2012/0014582 A1 | 1/2012 | Schaefer et al. |
| 2012/0207370 A1 | 8/2012 | Fahimian et al. |
| 2012/0263360 A1 | 10/2012 | Zhu et al. |
| 2012/0294504 A1 | 11/2012 | Kyriakou |
| 2013/0101082 A1 | 4/2013 | Jordan et al. |
| 2013/0294570 A1 | 11/2013 | Hansis |
| 2014/0018671 A1 | 1/2014 | Li et al. |
| 2014/0086383 A1 | 3/2014 | Huwer et al. |
| 2014/0169652 A1 | 6/2014 | Vic et al. |
| 2015/0297165 A1 | 10/2015 | Tanaka et al. |
| 2015/0305696 A1 | 10/2015 | Tamakawa et al. |
| 2016/0016009 A1 | 1/2016 | Manzke et al. |
| 2016/0120486 A1 | 5/2016 | Goto et al. |
| 2016/0220844 A1 | 8/2016 | Paysan et al. |
| 2016/0262709 A1 | 9/2016 | Siewerdsen et al. |
| 2017/0000428 A1 | 1/2017 | Goto |
| 2017/0197098 A1 | 7/2017 | Hirasawa et al. |
| 2017/0205360 A1 | 7/2017 | Cinquin et al. |
| 2017/0278277 A1 | 9/2017 | Morf et al. |
| 2017/0332982 A1 | 11/2017 | Koehler et al. |
| 2018/0028143 A1 | 2/2018 | Wiggers et al. |
| 2018/0070894 A1 | 3/2018 | Osaki et al. |
| 2018/0192978 A1 | 7/2018 | Naylor |
| 2018/0345042 A1 | 12/2018 | Voronenko et al. |
| 2019/0099149 A1* | 4/2019 | Li ........................ A61B 6/4021 |
| 2020/0016432 A1 | 1/2020 | Maolinbay |
| 2020/0121267 A1* | 4/2020 | Deutschmann ........ A61B 6/105 |
| 2020/0402644 A1 | 12/2020 | Zhou et al. |
| 2021/0165122 A1 | 6/2021 | Morton |

FOREIGN PATENT DOCUMENTS

| | | |
|---|---|---|
| EP | 2383702 A1 | 11/2011 |
| JP | H09 218939 A | 8/1997 |
| JP | 2004 136021 | 5/2004 |
| JP | 2008 036275 | 2/2008 |
| WO | 2005112753 A2 | 12/2005 |
| WO | 2006/078386 A2 | 7/2006 |
| WO | 2010/014288 A1 | 2/2010 |
| WO | 2010/099621 A1 | 9/2010 |
| WO | 2015103184 A1 | 7/2015 |
| WO | 2018/156968 A1 | 8/2018 |
| WO | 2018/183748 A1 | 10/2018 |

OTHER PUBLICATIONS

Office Action from U.S. Appl. No. 16/694,190 dated Mar. 26, 2021, 9 pages.
Notice of Allowance from U.S. Appl. No. 16/694,190 dated Jun. 23, 2021, 8 pages.
Office Action from U.S. Appl. No. 16/694,192 dated Jun. 10, 2021, 10 pages.
Office Action from U.S. Appl. No. 16/694,202 dated Apr. 9, 2021, 12 pages.
Office Action from U.S. Appl. No. 16/694,218 dated Apr. 15, 2021, 7 pages.
Office Action from U.S. Appl. No. 16/694,230 dated Apr. 1, 2021, 6 pages.

(56) References Cited

OTHER PUBLICATIONS

Clackdoyle, et al., Data consistency conditions for truncated fanbeam and parallel projections, Med. Phys. Feb. 2015, pp. 831-845, vol. 42, No. 2.
Defrise, et al., A solution to the long-object problem in helical cone-beam tomography, Physics in Medicine and Biology, 2000, pp. 623-643, vol. 45.
Hsieh, et al., A novel reconstruction algorithm to extend the CT scan field-of-view, Med. Phys., Sep. 2004, pp. 2385-2391, vol. 31, No. 9.
Katsevich, A., An improved exact filtered backprojection algorithm for spiral computed tomography, Advances in Applied Mathematics, 2004, pp. 691-697, vol. 32.
Kudo et al., Exact and approximate algorithms for helical cone-beam CT, Physics in Medicine and Biology, 2004, pp. 1-26, vol. 49, No. 13.
Kunze, et al., Cone beam reconstruction with displaced flat panel detector, 10th International Meeting on Fully Three-Dimensional Image Reconstruction in Radiology and Nuclear Medicine, 2009, pp. 138-141.
Li et al., Scatter kernel estimation with an edge-spread function method for cone-beam computed tomography imaging Physics in Medicine and Biology, pp. 6729-6748, vol. 51.
Maslowski, et al., Acuros CTS: A fast, linear Boltzmann transport equation solver for computed tomography scatter—Part I: Core algorithms and validation, Med. Phys., 2018, pp. 1-15.
Ning, et al., X-ray scatter correction algorithm for cone beam CT imaging, Med. Phys., May 2004, pp. 1195-1202, vol. 31, No. 5.
Noo et al., A new scheme for view-dependent data differentiation in fan-beam and cone-beam computed tomography, Physics in Medicine and Biology, 2007, pp. 5593-5414, vol. 52.
Schäfer, et al., FBP and BPF reconstruction methods for circular X-ray tomography with off-center detector, Med. Phys., Jul. 2011, pp. S85-S94, vol. 38, No. 7.
Schäfer, et al., Cone-beam filtered back-projection for circular X-ray tomography with off-center detector, 10th International Meeting on Fully Three-Dimensional Image Reconstruction in Radiology and Nuclear Medicine, 2009, pp. 86-89.
Siewerdsen, et al., A simple, direct method for x-ray scatter estimation and correction in digital radiography and cone-beam CT, Med. Phys., Jan. 2006, pp. 187-197, vol. 33, No. 1.
Sun, et al., Improved scatter correction using adaptive scatter kernel superposition, Physics in Medicine and Biology, Oct. 2010, pp. 6695-6720, vol. 55.
Tang, et al., A sinogram extrapolation method for CT field of view extension, Proceedings of the Fifth CT Meeting, 2018, pp. 206-209.
Yu, et al., Radiation dose reduction in computed tomography: techniques and future perspective, Imaging Med., Oct. 2009, pp. 65-84, vol. 1.
Zamyatin, et al., Helical cone beam CT with an asymmetrical detector, Medical Physics, Oct. 2005, pp. 3117-3127, vol. 32, No. 10.
Zbijewski, et al., Efficient Monte Carlo Based Scatter Artifact Reduction in Cone-Beam Micro-CT, IEEE Transactions an Medical Imaging, Jul. 2006, pp. 817-827, vol. 25, No. 7.
Zhu, et al., Scatter Correction Method for X-ray CT Using Primary Modulation: Theory and Preliminary Results, IEEE Transactions on Medical Imaging, Dec. 2006, pp. 1573-1587, vol. 25, No. 12.
International Search Report and Written Opinion from PCT/US2019/063080 dated Mar. 16, 2020.
International Search Report and Written Opinion from PCT/US2019/063071 dated Mar. 18, 2020.
International Search Report and Written Opinion from PCT/US2019/063073 dated Apr. 3, 2020.
International Search Report and Written Opinion from PCT/US2019/063078 dated Oct. 8, 2020.
International Search Report and Written Opinion from PCT/US2019/063083 dated Mar. 16, 2020.
International Search Report and Written Opinion from PCT/US2019/063085 dated Mar. 16, 2020.
Invitation to Pay Additional Fees from PCT/US2019/063086 dated Mar. 26, 2020.
International Search Report and Written Opinion from PCT/US2019/063087 dated Apr. 3, 2020.
International Search Report and Written Opinion from PCT/US2019/063077 dated Mar. 16, 2020.
International Search Report and Written Opinion from PCT/US2019/063076 dated Mar. 16, 2020.
International Search Report and Written Opinion from PCT/US2019/063074 dated Mar. 23, 2020.
International Search Report and Written Opinion from PCT/US2019/063086 dated Nov. 16, 2020.
Kang et al., "Accurate for Head and Neck Cancer Patients Using 2D and 3D Image Guidance", Journal of Applied Clinical Medical Physics, vol. 12, No. 1, Dec. 1, 2011, pp. 86-96, XP055734549.
Ramamurthi et al., "Region of Interest Cone Beam Tomography With Prior CT Data," Conference Record of the 37th Asilomar Conference on Signals, Systems, & Computers, vol. 2, Nov. 9, 2003, pp. 1924-1927.
Spearman, et al. Effect of Automated Attenuation-Based Tube Voltage Selection on Radiation Dose at CT: An Observational Study on a Global Scale11 , Radiology, vol. 279, No. Apr. 1, 2016 (Apr. 1, 2016), pp. 167-174, XP055734550.
Vinson et al., "X-Ray Micro-CT With a Displaced Detector Array: Application to Helical Cone-Beam Reconstruction," Medical Physics, vol. 30, No. 10, Oct. 1, 2003, pp. 2758-2761.
Wang et al., "A General Cone-Beam Reconstruction Algorithm," IEEE Transactions on Medical Imaging, vol. 12, No. 3, Sep. 1, 1993.
Wang, "X-Ray Micro-CT With a Displaced Detector Array," Medical Physics, vol. 29, No. 7, Jul. 1, 2002.
Office Action from U.S. Appl. No. 16/694,161 dated Sep. 13, 2021, 18 pages.
Zhu, et al. Noise suppression in scatter correction for cone-beam CT, American Association of Physicists in Medicine, 2009, pp. 741-752, vol. 36, No. 3.
Anas, et al., High-quality 3D correction of ring and radiant artifacts in flat panel detector-based cone volume CT imaging, Phys. Med. Biol., 2011, pp. 6495-6519, vol. 56.
Bootsma, et al., Spatial frequency spectrum of the x-ray scatter distribution in CBCT projections, Med. Phys., Nov. 2013, pp. 111901-1-111901-15, vol. 40, No. 11.
International Search Report and Written Opinion from PCT/US2021/039824 dated Mar. 4, 2022.
International Search Report and Written Opinion from PCT/US2021/042906 dated Mar. 21, 2022.
Rührnschopf, et al., A general framework and review of scatter correctons methods in cone beam CT. Part 2: Scatter estimation approaches, Med. Phys. Sep. 2011, pp. 5186-5199, vol. 38, No. 9.
Yang, et al., Scattering sctimation for cone-Beam CT Using Local Measurement Based on Compressed Sensing, IEEE transactions on Nuclear Science, Mar. 2018, pp. 941-949, vol. 65, No. 3.

* cited by examiner

ASYMMETRIC SCATTER FITTING FOR OPTIMAL PANEL READOUT IN CONE-BEAM COMPUTED TOMOGRAPHY

CROSS-REFERENCE TO RELATED APPLICATIONS

This application claims the benefit of eleven U.S. provisional patent applications, including Ser. No. 62/773,712, filed Nov. 30, 2018; Ser. No. 62/773,700, filed Nov. 30, 2018; Ser. No. 62/796,831, filed Jan. 25, 2019; Ser. No. 62/800,287, filed Feb. 1, 2019; Ser. No. 62/801,260, filed Feb. 5, 2019; Ser. No. 62/813,335, filed Mar. 4, 2019; Ser. No. 62/821,116, filed Mar. 20, 2019; Ser. No. 62/836,357, filed Apr. 19, 2019; Ser. No. 62/836,352, filed Apr. 19, 2019; Ser. No. 62/843,796, filed May 6, 2019; and Ser. No. 62/878,364, filed Jul. 25, 2019. This application is also related to ten non-provisional U.S. patent applications filed on the same day, including Ser. No. 16/694,145, filed Nov. 25, 2019, entitled "MULTIMODAL RADIATION APPARATUS AND METHODS;" Ser. No. 16/694,148, filed Nov. 25, 2019, entitled "APPARATUS AND METHODS FOR SCALABLE FIELD OF VIEW IMAGING USING A MULTI-SOURCE SYSTEM;" Ser. No. 16/694,161, filed Nov. 25, 2019, entitled "INTEGRATED HELICAL FAN-BEAM COMPUTED TOMOGRAPHY IN IMAGE-GUIDED RADIATION TREATMENT DEVICE;" Ser. No. 16/694,166, filed Nov. 25, 2019, entitled "COMPUTED TOMOGRAPHY SYSTEM AND METHOD FOR IMAGE IMPROVEMENT USING PRIOR IMAGE;" Ser. No. 16/694,177, filed Nov. 25, 2019, entitled "OPTIMIZED SCANNING METHODS AND TOMOGRAPHY SYSTEM USING REGION OF INTEREST DATA;" Ser. No. 16/694,190, filed Nov. 25, 2019, entitled "HELICAL CONE-BEAM COMPUTED TOMOGRAPHY IMAGING WITH AN OFF-CENTERED DETECTOR;" Ser. No. 16/694,192, filed Nov. 25, 2019, entitled "MULTI-PASS COMPUTED TOMOGRAPHY SCANS FOR IMPROVED WORKFLOW AND PERFORMANCE;" Ser. No. 16/694,202, filed Nov. 25, 2019, entitled "METHOD AND APPARATUS FOR SCATTER ESTIMATION IN CONE-BEAM COMPUTED TOMOGRAPHY;" Ser. No. 16/694,218, filed Nov. 25, 2019, entitled "METHOD AND APPARATUS FOR IMPROVING SCATTER ESTIMATION AND CORRECTION IN IMAGING;" and Ser. No. 16/694,230, filed Nov. 25, 2019, entitled "METHOD AND APPARATUS FOR IMAGE RECONSTRUCTION AND CORRECTION USING INTER-FRACTIONAL INFORMATION." The contents of all above-identified patent application(s) and patent(s) are fully incorporated herein by reference.

FIELD OF THE INVENTION

Aspects of the disclosed technology relate to estimating scatter in projection data, and, more particularly, to utilizing shadow region data, including asymmetric shadow regions/data, from a detector readout to estimate scatter in primary region projection data, including during cone-beam computed tomography (CT) scans.

BACKGROUND

Scatter in cone-beam CT can account for a significant portion of the detected photons when no anti-scatter grids are used with a wide collimation opening. Scatter can negatively impact image quality, including contrast and quantitative accuracy. Consequently, scatter measurement, estimation, and correction are applicable to cone-beam CT data processing and image reconstruction, including in the context of image-guided radiation treatment (IGRT). IGRT can make use of medical imaging technology, such as CT, to collect images of a patient before, during, and/or after treatment.

Fitting the data in collimator shadows to predict the scatter in the opening is an effective scatter estimation approach for cone-beam CT (CBCT). Conventionally, this approach needs a significant amount of data in the collimator shadows from both sides of the primary region for reliable scatter fitting. Furthermore, a reduced detector (panel) readout range can be desirable to reduce the readout time to allow scans with higher frame rates.

BRIEF SUMMARY

In one embodiment, estimating scatter in x-ray images includes receiving measured projection data from a primary region of an x-ray detector, wherein the primary region of the x-ray detector is directly exposed to a radiation beam from a radiation source during at least one scan, receiving measured scatter data from at least one shadow region of the x-ray detector, wherein the at least one shadow region of the x-ray detector is blocked from direct exposure to the radiation beam, and determining an estimated scatter in the measured projection data based on the measured scatter data in the at least one shadow region, wherein an aperture center of the primary region is offset from a readout center of the readout range during the at least one scan.

Features that are described and/or illustrated with respect to one embodiment may be used in the same way or in a similar way in one or more other embodiments and/or in combination with or instead of the features of the other embodiments.

The descriptions of the invention do not limit the words used in the claims in any way or the scope of the claims or invention. The words used in the claims have all of their full ordinary meanings.

BRIEF DESCRIPTION OF THE DRAWINGS

In the accompanying drawings, which are incorporated in and constitute a part of the specification, embodiments of the invention are illustrated, which, together with a general description of the invention given above, and the detailed description given below, serve to exemplify embodiments of this invention. It will be appreciated that illustrated element boundaries (e.g., boxes, groups of boxes, or other shapes) in the figures represent one embodiment of boundaries. In some embodiments, one element may be designed as multiple elements or that multiple elements may be designed as one element. In some embodiments, an element shown as an internal component of another element may be implemented as an external component and vice versa. Furthermore, elements may not be drawn to scale.

DETAILED DESCRIPTION

Figure 1:
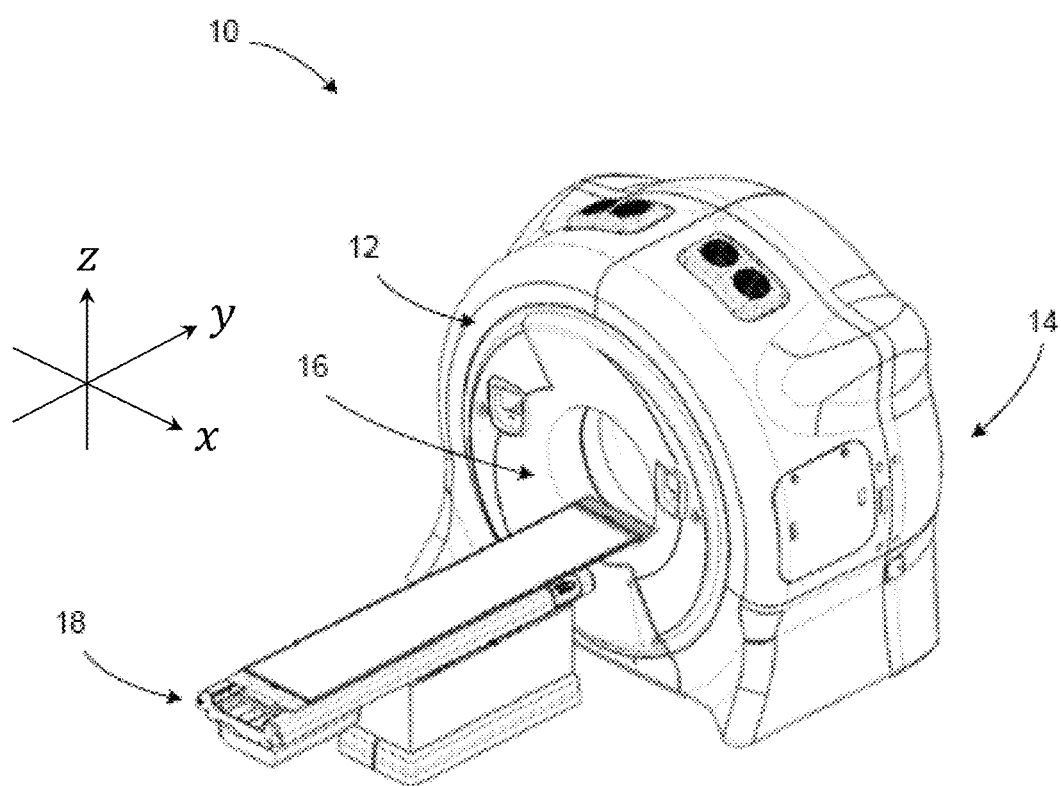
FIG. 1 is a perspective view of an exemplary x-ray imaging apparatus in accordance with one aspect of the disclosed technology.

The following includes definitions of exemplary terms that may be used throughout the disclosure. Both singular and plural forms of all terms fall within each meaning.

"Component," as used herein can be defined as a portion of hardware, a portion of software, or a combination thereof. A portion of hardware can include at least a processor and a portion of memory, wherein the memory includes an instruction to execute. A component may be associated with a device.

"Logic," synonymous with "circuit" as used herein, includes but is not limited to hardware, firmware, software and/or combinations of each to perform a function(s) or an action(s). For example, based on a desired application or needs, logic may include a software-controlled microprocessor, discrete logic such as an application specific integrated circuit (ASIC), or other programmed logic device and/or controller. Logic may also be fully embodied as software.

"Processor," as used herein includes, but is not limited to, one or more of virtually any number of processor systems or stand-alone processors, such as microprocessors, microcontrollers, central processing units (CPUs), and digital signal processors (DSPs), in any combination. The processor may be associated with various other circuits that support operation of the processor, such as random access memory (RAM), read-only memory (ROM), programmable read-only memory (PROM), erasable programmable read-only memory (EPROM), clocks, decoders, memory controllers, or interrupt controllers, etc. These support circuits may be internal or external to the processor or its associated electronic packaging. The support circuits are in operative communication with the processor. The support circuits are not necessarily shown separate from the processor in block diagrams or other drawings.

"Signal," as used herein includes, but is not limited to, one or more electrical signals, including analog or digital signals, one or more computer instructions, a bit or bit stream, or the like.

"Software", as used herein, includes but is not limited to one or more computer readable and/or executable instructions that cause a computer, processor, logic, and/or other electronic device to perform functions, actions, and/or behave in a desired manner. The instructions may be embodied in various forms such as routines, algorithms, modules, or programs including separate applications or code from dynamically linked sources or libraries.

While the above exemplary definitions have been provided, it is Applicant's intention that the broadest reasonable interpretation consistent with this specification be used for these and other terms.

As is discussed in more detail below, embodiments of the disclosed technology relate to estimating scatter in imaging projection data, including utilizing shadow region data to estimate scatter in primary region projection data during cone-beam CT scans. In some embodiments, a radiotherapy delivery device and method can make use of an integrated low-energy radiation source for CT for use in conjunction with or as part of IGRT. In particular, for example, a radiotherapy delivery device and method can combine a low-energy collimated radiation source for imaging in a gantry using rotational (e.g., helical or step-and-shoot) image acquisition along with a high-energy radiation source for therapeutic treatment.

The low-energy radiation source (e.g., kilovolt (kV)) can produce higher quality images than via use of the high-energy radiation source (e.g., megavolt (MV)) for imaging. Images generated with kV energy typically have better tissue contrast than with MV energy. High quality volume imaging can be needed for visualization of targets and organs-at-risk (OARS), for adaptive therapy monitoring, and for treatment planning/re-planning. In some embodiments, the kV imaging system can also be used for positioning, motion tracking, and/or characterization or correction capabilities.

The image acquisition methodology can include or otherwise make use of a multiple rotation scan, which may be, for example, a continuous scan (e.g., with a helical source trajectory about a central axis together with longitudinal movement of a patient support through a gantry bore), a non-continuous circular stop-and-reverse scan with incremental longitudinal movement of a patient support, step-and-shoot circular scans, etc.

In accordance with various embodiments, the imaging apparatus collimates a radiation source, including, for example, into a cone beam or a fan beam using, for example, a beamformer. In one embodiment, the collimated beam can be combined with a gantry that continuously rotates while the patient moves, resulting in a helical image acquisition.

In some embodiments, the time associated with increased scanning rotations to complete a high-quality volume image may be mitigated by high gantry rates/speed (e.g., using fast slip ring rotation, including, e.g., up to 10 revolutions per minute (rpm), up to 20 rpm, up to 60 rpm, or more rpm), high kV frame rates, and/or sparse data reconstruction techniques, to provide kV CT imaging on a radiation therapy delivery platform. Detectors (with various row/slice sizes, configurations, dynamic range, etc.), scan pitch, and/or dynamic collimation are additional features in various embodiments, including to selectively expose portions of the detector and selectively define active readout areas, as discussed in detail below. In particular, image quality can be improved (by estimating the scatter as described below) by using an adjustable beamformer/collimator on the x-ray (low-energy) imaging radiation source and/or optimizing the detector readout range.

The imaging apparatus and method can provide selective and variable collimation of a radiation beam emitted by the source of radiation, including adjusting the radiation beam shape to expose less than the entire active area of an associated radiation detector (e.g., a radiation detector positioned to receive radiation from the x-ray radiation source). For example, a beamformer of the imaging apparatus can adjust the shape of the radiation beam as the pitch varies during a helical scan. Exposing only a primary region of the detector to direct radiation allows shadowed regions of the detector to receive only scatter. Scatter measurements in the shadow region (and in some embodiments measurements in the penumbra region) of the detector can be used to estimate scatter in the primary region of the detector receiving projection data.

The imaging apparatus and method can provide selective and variable detector readout areas and ranges, including adjusting the detector readout range to limit the active area of the detector for improved readout speed. For example, less than the available shadow region data may be read and used for scatter estimation. Combining selective readout with beamforming allows for various optimizations of scatter fitting techniques.

Figure 2:
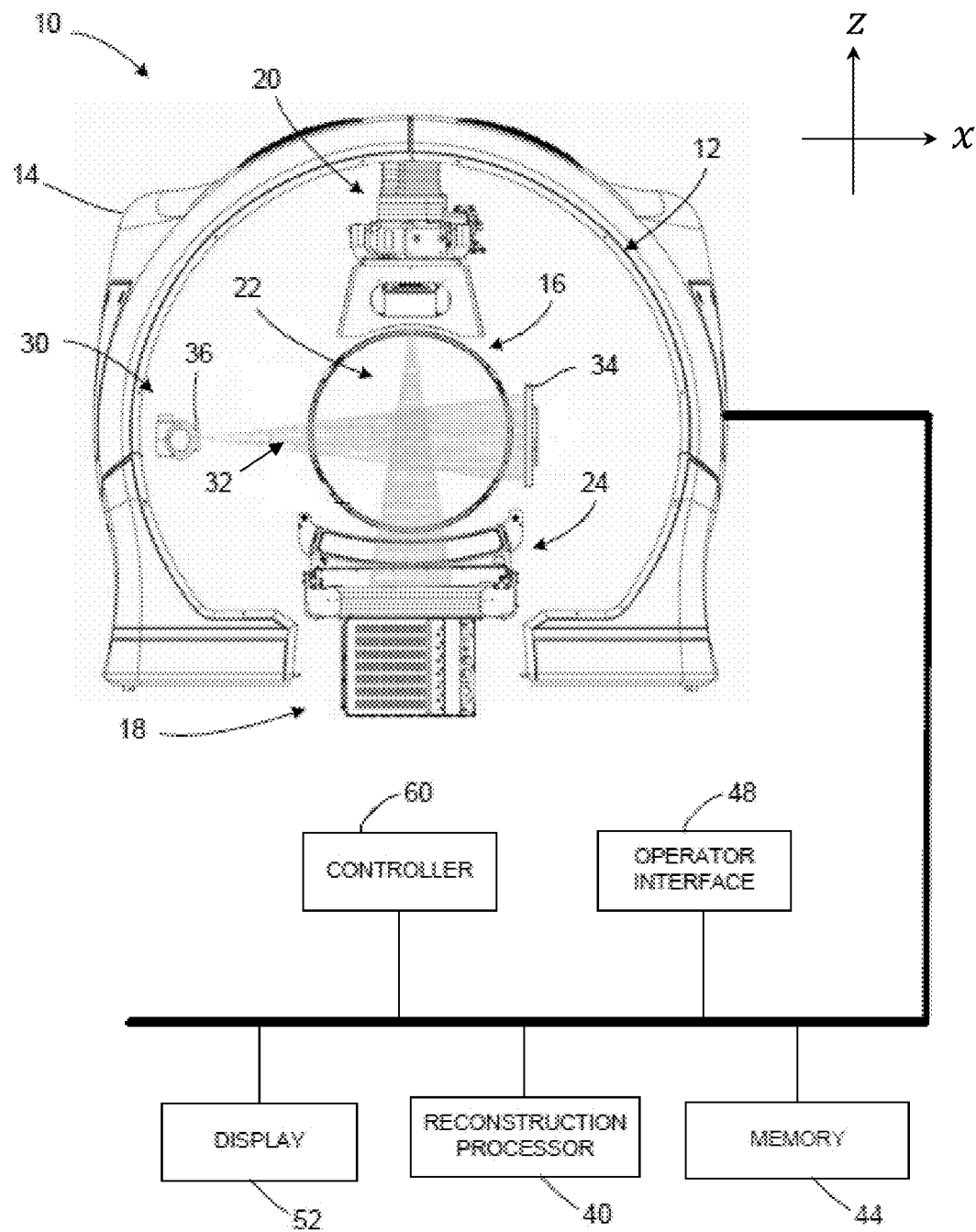
FIG. 2 is a diagrammatic illustration of an x-ray imaging apparatus integrated into an exemplary radiotherapy device in accordance with one aspect of the disclosed technology.

With reference to FIG. 1 and FIG. 2, an imaging apparatus 10 (e.g., an x-ray imaging apparatus) is shown. It will be appreciated that the x-ray imaging apparatus 10 may be associated with and/or integrated into a radiotherapy device (as shown in FIG. 2) that can be used for a variety of applications, including, but not limited to IGRT. The x-ray imaging apparatus 10 includes a rotatable gantry system, referred to as gantry 12 supported by or otherwise housed in a support unit or housing 14. Gantry herein refers to a gantry system that comprises one or more gantries (e.g., ring or C-arm) capable of supporting one or more radiation sources and/or associated detectors as they rotate around a target. For example, in one embodiment, a first radiation source and its associated detector may be mounted to a first gantry of the gantry system and a second radiation source and its associated detector may be mounted to a second gantry of the gantry system. In another embodiment, more than one radiation source and associated detector(s) may be mounted to the same gantry of the gantry system, including, for example, where the gantry system is comprised of only one gantry. Various combinations of gantries, radiation sources, and radiation detectors may be combined into a variety of gantry system configurations to image and/or treat the same volume within the same apparatus. For example, kV and MV radiation sources can be mounted on the same or different gantries of the gantry system and selectively used for imaging and/or treatment as part of an IGRT system. If mounted to different gantries, the radiation sources are able to rotate independently, but are still able to simultaneously image the same (or nearly the same) volume. A rotatable ring gantry 12 may be capable of 10 rpm or more, as mentioned above. The rotatable gantry 12 defines a gantry bore 16 into and through which a patient can be moved and positioned for imaging and/or treatment. In accordance with one embodiment, the rotatable gantry 12 is configured as a slip ring gantry to provide continuous rotation of an imaging radiation source (x-ray) and an associated radiation detector while providing sufficient bandwidth for the high-quality imaging data received by the detector. A slip-ring gantry can eliminate gantry rotations in alternating directions in order to wind and unwind cables carrying the power and signals associated with the device. Such a configuration will allow for continuous helical computed tomography, including CBCT, even when integrated into an IGRT system.

A patient support 18 is positioned adjacent to the rotatable gantry 12 and configured to support a patient, typically in a horizontal position, for longitudinal movement into and within the rotatable gantry 12. The patient support 18 can move the patient, for example, in a direction perpendicular to the plane of rotation of the gantry 12 (along or parallel to the rotation axis of the gantry 12). The patient support 18 can be operatively coupled to a patient support controller for controlling movement of the patient and patient support 18. The patient support controller can be synchronized with the rotatable gantry 12 and sources of radiation mounted to the rotating gantry for rotation about a patient longitudinal axis in accordance with a commanded imaging and/or treatment plan. The patient support can also be moved in a limited range up and down, left and right once it is in the bore 16 to adjust the patient position for optimal treatment. Axes x, y, and z are shown, where, viewing from the front of the gantry 12, the x-axis is horizontal and points to the right, the y-axis points into the gantry plane, and the z-axis is vertical and points to the top. The x-, y-, and z-axes follow the right-hand rule.

It will be appreciated that other variations can be employed without departing from the scope of the disclosed technology. For example, the rotatable gantry 12 and patient support 18 can be controlled such that the gantry 12 rotates in a "back-and-forth" manner (e.g., alternating clockwise rotation and counterclockwise rotation) around a patient supported on the patient support (as opposed to continuously, as is described above) as the support is controlled to move (at a constant or variable speed) relative to the rotatable gantry 12. In another embodiment, with successive step-and-shoot circular scans, movement of the patient support 18 in the longitudinal direction (step) alternates with a scanning revolution by the rotatable gantry 12 (shoot) until the desired volume is captured. The device 10 is capable of volume-based and planar-based imaging acquisitions. For example, in various embodiments, the device 10 may be used to acquire volume images and/or planar images and execute the associated processing methods described below.

Various other types of radiation source and/or patient support movement may be utilized to achieve relative motion of the radiation source and the patient for generation of projection data. Non-continuous motion of the radiation source and/or patient support, continuous but variable/non-constant (including linear and non-linear) linear movement, speed, and/or trajectories, etc., and combinations thereof may be used, including in combination with the various embodiments of radiotherapy devices 10 described above.

As shown in FIG. 2, the x-ray imaging apparatus 10 includes a source of imaging radiation 30 coupled to or otherwise supported by the rotatable gantry 12. The source of imaging radiation 30 emits a radiation beam (indicated generally as 32) for generating high-quality images. In this embodiment, the source of imaging radiation is an x-ray source 30, configured as a kilovoltage (kV) source (e.g., a clinical x-ray source having an energy level in the range of about 20 kV to about 150 kV). In one embodiment, the kV source of radiation comprises a kilo-electron volt peak photon energy (keV) up to 150 keV. The imaging radiation source can be any type of transmission source suitable for imaging. For example, the imaging radiation source may be, for example, an x-ray generating source (including for CT) or any other way to produce photons with sufficient energy and flux (such as, e.g., a gamma-source (e.g., Cobalt-57, energy peak at 122 keV), an x-ray fluorescence source (such as fluorescence source through Pb k lines, two peaks @about 70 keV and @about 82 keV), etc.). References herein to x-ray, x-ray imaging, x-ray imaging source, etc. are exemplary for particular embodiments. Other imaging transmission sources can be used interchangeably in various other embodiments.

The x-ray imaging apparatus 10 also can include another source of radiation 20 coupled to or otherwise supported by the rotatable gantry 12. In accordance with one embodiment, the source of radiation 20 is configured as a source of therapeutic radiation, such as a high-energy source of radiation used for treatment of a tumor within a patient in a region of interest. It will be appreciated that the source of therapeutic radiation can be a high-energy x-ray beam (e.g., megavoltage (MV) x-ray beam), and/or a high-energy particle beam (e.g., a beam of electrons, a beam of protons, or a beam of heavier ions, such as carbon) or another suitable form of high-energy radiation without departing from the scope of the disclosed technology. In one embodiment, the source of radiation 20 comprises a mega-electron volt peak photon energy (MeV) of 1 MeV or greater. In one embodiment, the high-energy x-ray beam has an average energy greater than 0.8 MeV. In another embodiment, the high-energy x-ray beam has an average energy greater than 0.2 MeV. In another embodiment, the high-energy x-ray beam has an average energy greater than 150 keV. Generally, the source of radiation 20 has a higher energy level (peak and/or average, etc.) than the source of imaging radiation 30.

In one embodiment, the source of radiation 20 is a LINAC producing therapeutic radiation (e.g., MV) and the imaging system comprises an independent source of imaging radiation 30 producing relatively low intensity and lower energy imaging radiation (e.g., kV). In other embodiments, the source of radiation 20 could be a radioisotope, such as, for example, Co-60, which can generally have energy >1 MeV. The source of radiation 20 can emit one or more beams of radiation (indicated generally by 22) toward a region-of-interest (ROI) within a patient supported on the patient support 18 in accordance with a treatment plan.

In some embodiments, sources of radiation 20, 30 may be used in conjunction with one another to provide higher quality and better utilized images. In other embodiments, at least one additional radiation source can be coupled to the rotatable gantry 12 and operated to acquire projection data at a peak photon energy distinct from the peak photon energies of sources of radiation 20, 30.

Although FIGS. 1 and 2 depict an x-ray imaging apparatus 10 with a radiation source 30 mounted to a ring gantry 12, other embodiments may include other types of rotatable imaging apparatuses, including, for example, C-arm gantries and robotic arm-based systems. In gantry-based systems, a gantry rotates the imaging radiation source 30 around an axis passing through the isocenter. Gantry-based systems include C-arm gantries, in which the imaging radiation source 30 is mounted, in a cantilever-like manner, over and rotates about the axis passing through the isocenter. Gantry-based systems further include ring gantries, for example, rotatable gantry 12, having generally toroidal shapes in which the patient's body extends through a bore of the ring/toroid, and the imaging radiation source 30 is mounted on the perimeter of the ring and rotates about the axis passing through the isocenter. In some embodiments, the gantry 12 rotates continuously. In other embodiments, the gantry 12 utilizes a cable-based system that rotates and reverses repeatedly.

A detector 34 (e.g., two-dimensional flat detector or curved detector) can be coupled to or otherwise supported by the rotatable gantry 12. The detector 34 (e.g., x-ray detector) is positioned to receive radiation from the x-ray source 30 and can rotate along with the x-ray source 30. The detector 34 can detect or otherwise measure the amount of radiation not attenuated and therefore infer what was in fact attenuated by the patient or associated patient ROI (by comparison to what was initially generated). The detector 34 can detect or otherwise collect attenuation data from different angles as the radiation source 30 rotates around and emits radiation toward the patient.

It will be appreciated that the detector 34 can take on a number of configurations without departing from the scope of the disclosed technology. As illustrated in FIG. 2, the detector 34 can be configured as a flat-panel detector (e.g., a multi-row flat panel detector). In accordance with another exemplary embodiment, the detector 34 can be configured as a curved detector.

A collimator or beamformer assembly (indicated generally as 36) is positioned relative to the imaging (x-ray) source 30 to selectively control and adjust a shape of a radiation beam 32 emitted by the x-ray source 30 to selectively expose a portion or region of the active area of the detector 34. The beamformer can also control how the radiation beam 32 is positioned on the detector 34. In one embodiment, the beamformer 36 could have one degree/dimension of motion (e.g., to make a thinner or fatter slit). In another embodiment, the beamformer 36 can have two degrees/dimensions of motion (e.g., to make various sized rectangles). In other embodiments, the beamformer 36 may be capable of various other dynamically-controlled shapes, including, for example, parallelograms. All of these shapes may be dynamically adjusted during a scan. In some embodiments, blocking portions of the beamformer can be rotated and translated.

The beamformer 36 can be controlled to adjust the shape of the radiation beam 32 emitted by the x-ray source 30 dynamically in a number of geometries, including, but not limited to, a fan beam or cone beam having a beam thickness (width) as low as one detector row width or including multiple detector rows, which will be only a portion of the detector's active area. In various embodiments, the thickness of the beam may expose several centimeters of a larger detector active area. For example, 3-4 centimeters (measured in the longitudinal direction in the detector plane) of a 5-6 centimeter detector may be selectively exposed to the imaging radiation 32. In this embodiment, 3-4 centimeters of projection image data may be captured with each readout, with about 1-2 centimeters of unexposed detector area on one or each side, which may be used to capture scatter data, as discussed below.

In other embodiments, more or less of a portion of the active detector may be selectively exposed to the imaging radiation. For example, in some embodiments, the beam thickness may be reduced down to about two centimeters, one centimeter, less than one centimeter, or ranges of similar sizes, including with smaller detectors. In other embodiments, the beam thickness may be increased to about 4 centimeters, 5 centimeters, greater than 5 centimeters, or ranges of similar sizes, including with larger detectors. In various embodiments, the ratio of exposed-to-active detector area may be 30-90% or 50-75%. In other embodiments, the ratio of exposed-to-active detector area may be 60-70%. However, various other exposed and active area sizes or ratios of exposed-to-active detector area may be suitable in other embodiments. The beam and detector can be configured so that the shadowed region of the detector (active but not exposed to direct radiation) is sufficient to capture scatter data beyond the penumbra region.

Various embodiments may include an optimization of the features that control selective exposure of the detector (e.g., beam size, beam/aperture center, collimation, pitch, detector readout range, detector readout center, etc.) such that the measured data is sufficient for primary (exposed) and shadowed regions, but also optimized for speed and dosage control. The beamformer 36 shape/position and detector 34 readout range can be controlled such that the radiation beam 32 from the x-ray source 30 covers as much or as little of the x-ray detector 34 based on the particular imaging task and scatter estimation process being carried out. Generally, the active area of the detector 34 can be configured such that one or two asymmetric shadow regions of the x-ray detector 34 can be read along with the primary region.

The beamformer may be configured in a variety of ways that allow it to adjust the shape of the radiation beam 32 emitted by the x-ray source 30. For example, the collimator 36 can be configured to include a set of jaws or other suitable members that define and selectively adjust the size of an aperture through which the radiation beam from the x-ray source 30 may pass in a collimated manner. In accordance with one exemplary configuration, the collimator 36 can include an upper jaw and a lower jaw, where the upper and lower jaws are movable in different directions (e.g., parallel directions) to adjust the size of the aperture through which the radiation beam from the x-ray source 30 passes, and also to adjust the beam position relative to the patient to illuminate only the portion of the patient to be imaged for optimized imaging and minimized patient dose. For example, a collimator can be configured as a multi-leaf collimator (MLC), which can include a plurality of interlaced leaves operable to move to one or more positions between a minimally-open or closed position and a maximally-open position. It will be appreciated that the leaves can be moved into desired positions to achieve a desired shape of a radiation beam being emitted by the radiation source. In one embodiment, the MLC is capable of sub-millimeter targeting precision.

In accordance with one embodiment, the shape of the radiation beam 32 from the x-ray source 30 can be changed during an image acquisition. Stated differently, in accordance with one exemplary implementation, the beamformer 36 leaf positions and/or aperture width can be adjusted before or during a scan. For example, in accordance with one embodiment, the beamformer 36 can be selectively controlled and dynamically adjusted during rotation of the x-ray source 30 such that the radiation beam 32 has a shape with sufficient primary/shadow regions and is adjusted to include only an object of interest during imaging (e.g., the prostate). The shape of the radiation beam 32 being emitted by the x-ray source 30 can be changed during or after a scan, depending on the desired image acquisition, which may be based on imaging and/or therapeutic feedback, as discussed in more detail below.

Detector 24 can be coupled to or otherwise supported by the rotatable gantry 12 and positioned to receive radiation 22 from the therapeutic radiation source 20. The detector 24 can detect or otherwise measure the amount of radiation not attenuated and therefore infer what was in fact attenuated by the patient or associated patient ROI (by comparison to what was initially generated). The detector 24 can detect or otherwise collect attenuation data from different angles as the therapeutic radiation source 20 rotates around and emits radiation toward the patient.

It will be further appreciated that the therapeutic radiation source 20 can include or otherwise be associated with a beamformer or collimator. The collimator/beamformer associated with the therapeutic radiation source 20 can be configured in a number of ways, similar to the collimator/beamformer 36 associated with the imaging source 30.

The therapeutic radiation source 20 may be mounted, configured, and/or moved into the same plane or a different plane (offset) than the imaging source 30. In some embodiments, scatter caused by simultaneous activation of the radiation sources 20, 30 may be reduced by offsetting the radiation planes.

When integrated with a radiotherapy device, imaging apparatus 10 can provide images that are used to set up (e.g., align and/or register), plan, and/or guide a radiation delivery procedure (treatment). Typical set-up is accomplished by comparing current (in-treatment) images to pre-treatment image information. Pre-treatment image information may comprise, for example, x-ray, CT data, CBCT data, magnetic resonance imaging (MRI) data, positron emission tomography (PET) data or 3D rotational angiography (3DRA) data, and/or any information obtained from these or other imaging modalities. In some embodiments, the imaging apparatus 10 can track in-treatment patient, target, or ROI motion.

A reconstruction processor 40 can be operatively coupled to detector 24 and/or x-ray detector 34. In one embodiment, the reconstruction processor 40 is configured to generate patient images based on radiation received by detectors 24, 34 from the radiation sources 20, 30. It will be appreciated that the reconstruction processor 40 can be configured to be used to carry out the methods described more fully below. The apparatus 10 can also include a memory 44 suitable for storing information, including, but not limited to, processing and reconstruction algorithms and software, imaging parameters, image data from a prior or otherwise previously-acquired image (e.g., a planning image), treatment plans, and the like.

The imaging apparatus 10 can include an operator/user interface 48, where an operator of the imaging apparatus 10 can interact with or otherwise control the imaging apparatus 10 to provide input relating to scan or imaging parameters and the like. The operator interface 48 can include any suitable input devices, such as a keyboard, mouse, voice-activated controller, or the like. The imaging apparatus 10 can also include a display 52 or other human-readable element to provide output to the operator of the imaging apparatus 10. For example, the display 52 can allow the operator to observe reconstructed patient images and other information, such as imaging or scan parameters, related to operation of the imaging apparatus 10.

As shown in FIG. 2, the imaging apparatus 10 includes a controller (indicated generally as 60) operatively coupled to one or more components of the apparatus 10. The controller 60 controls the overall functioning and operation of apparatus 10, including providing power and timing signals to the imaging source 30 and/or the therapeutic radiation source 20 and a gantry motor controller that controls rotational speed and position of the rotatable gantry 12. It will be appreciated that the controller 60 can encompass one or more of the following: a patient support controller, a gantry controller, a controller coupled to the therapeutic radiation source 20 and/or the imaging source 30, a beamformer 36 controller, a controller coupled to the detector 24 and/or the detector 34, and the like. In one embodiment controller 60 is a system controller that can control other components, devices, and/or controllers.

In various embodiments, the reconstruction processor 40, the operator interface 48, the display 52, the controller 60 and/or other components may be combined into one or more components or devices.

The apparatus 10 may include various components, logic, and software. In one embodiment, the controller 60 comprises a processor, a memory, and software. By way of example and not limitation, an x-ray imaging apparatus and/or radiotherapy system can include various other devices and components (e.g., gantries, radiation sources, collimators, detectors, controllers, power sources, patient supports, among others) that can implement one or more routines or steps related to imaging and/or IGRT for a specific application, wherein a routine can include imaging, image-based pre-delivery steps, and/or treatment delivery, including respective device settings, configurations, and/or positions (e.g., paths/trajectories), which may be stored in memory. Furthermore, the controller(s) can directly or indirectly control one or more devices and/or components in accordance with one or more routines or processes stored in memory. An example of direct control is the setting of various radiation source or collimator parameters (power, speed, position, timing, modulation, etc.) associated with imaging or treatment. An example of indirect control is the communication of position, path, speed, etc. to a patient support controller or other peripheral device. The hierarchy of the various controllers that may be associated with an imaging apparatus can be arranged in any suitable manner to communicate the appropriate commands and/or information to the desired devices and components.

Moreover, those skilled in the art will appreciate that the systems and methods may be implemented with other computer system configurations. The illustrated aspects of the invention may be practiced in distributed computing environments where certain tasks are performed by local or remote processing devices that are linked through a communications network. For example, in one embodiment, the reconstruction processor 40 may be associated with a separate system. In a distributed computing environment, program modules may be located in both local and remote memory storage devices. For instance, a remote database, a local database, a cloud-computing platform, a cloud database, or a combination thereof can be utilized with imaging apparatus 10.

Imaging apparatus 10 can utilize an exemplary environment for implementing various aspects of the invention including a computer, wherein the computer includes the controller 60 (e.g., including a processor and a memory, which may be memory 44) and a system bus. The system bus can couple system components including, but not limited to the memory to the processor, and can communicate with other systems, controllers, components, devices, and processors. Memory can include read only memory (ROM), random access memory (RAM), hard drives, flash drives, and any other form of computer readable media. Memory can store various software and data, including routines and parameters, which may comprise, for example, a treatment plan.

The therapeutic radiation source 20 and/or imaging source 30 can be operatively coupled to a controller 60 configured to control the relative operation of the therapeutic radiation source 20 and the imaging source 30. For example, the imaging source 30 can be controlled and operated simultaneously with the therapeutic radiation source 20. In addition, or alternatively, the imaging source 30 can be controlled and operated sequentially with the therapeutic radiation source 20, depending on the particular treatment and/or imaging plan being implemented.

It will be appreciated that the imaging source 30 and the detector 34 can be configured to provide rotation around the patient during an imaging scan in a number of ways. In one embodiment, synchronizing the motion and exposure of the imaging source 30 with the longitudinal motion of the patient support 18 can provide a continuous helical acquisition of a patient image during a procedure. In addition to continuous rotation of the radiation sources 20, 30 and detector(s) 24, 34 (e.g., continuous and constant rotation of the gantry with constant patient motion speed), it will be appreciated that other variations can be employed without departing from the scope of the disclosed technology. For example, the rotatable gantry 12 and patient support can be controlled such that the gantry 12 rotates in a "back-and-forth" manner (e.g., alternating clockwise rotation and counterclockwise rotation) around a patient supported on the patient support (as opposed to continuously, as is described above) as the support is controlled to move (at a constant or variable speed) relative to the rotatable gantry 12. In another embodiment, with successive step-and-shoot circular scans, movement of the patient support 18 in the longitudinal direction (step) alternates with a scanning revolution by the rotatable gantry 12 (shoot) until the desired volume is captured. The imaging apparatus 10 is capable of volume-based and planar-based imaging acquisitions. For example, in various embodiments, the imaging apparatus 10 may be used to acquire volume images and/or planar images (e.g., via use of the imaging source 30 and the detector 34) and execute the associated processing, including scatter estimation/correction methods described below.

Various other types of radiation source and/or patient support movement may be utilized to achieve relative motion of the radiation source and the patient for generation of projection data. Non-continuous motion of the radiation source and/or patient support, continuous but variable/non-constant (including linear and non-linear) movement, speed, and/or trajectories, etc., and combinations thereof may be used, including in combination with the various embodiments of radiotherapy devices 10 described above.

In one embodiment, the gantry 12 rotation speed, the patient support 18 speed, the beamformer 36 shape, and/or the detector 34 readout could all be constant during image acquisition. In other embodiments, one or more of these variables could change dynamically during image acquisition. The gantry 12 rotation speed, patient support 18 speed, beamformer 36 shape, and/or detector 34 readout can be varied to balance different factors, including, for example, image quality and image acquisition time.

In other embodiments, these features can be combined with one or more other image-based activities or procedures, including, for example, patient set up, adaptive therapy monitoring, treatment planning, etc.

There are many determinants of image quality (e.g., imaging source focal spot size, detector dynamic range, etc.). A limitation of kV CBCT image quality is scatter. Various approaches can be used to reduce scatter. One approach is to use an anti-scatter grid (which collimates the scatter). However, it can be problematic to implement a scatter grid on a kV imaging system, including for motion tracking and correction. Accurately estimating scatter in the projection data is necessary to improve the quality of the image data. In various embodiments, scatter in the projection data acquired in a primary region of the detector 34 can be estimated based on data measured in shadow regions (and penumbra regions) of the detector 34.

Figure 3:
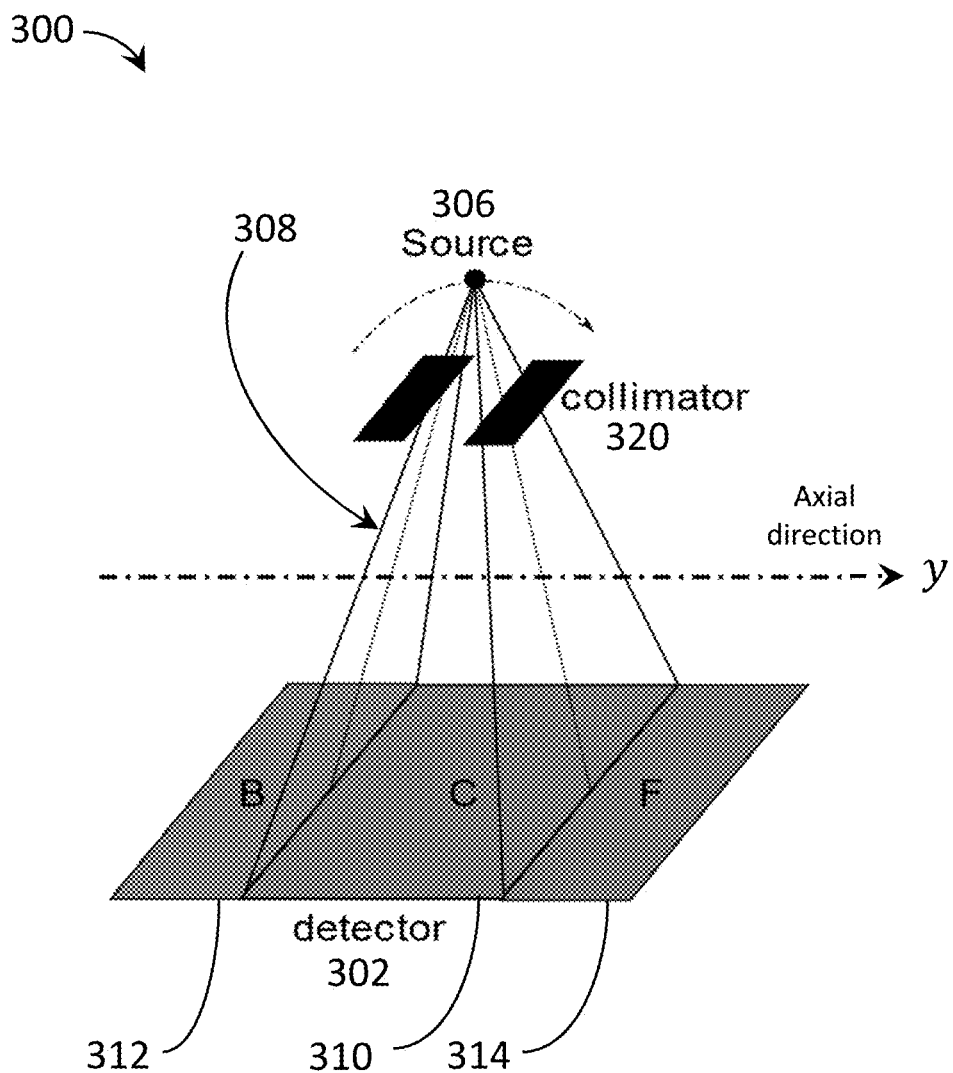
FIG. 3 is a diagrammatic illustration of an exemplary collimated projection onto an x-ray detector.

FIG. 3 is a diagrammatic illustration of an exemplary collimated projection 300 onto an x-ray detector 302. Rotating X-ray source 306 is shown emitting radiation beam 308 exposing a primary or center (C) region 310 of the detector 302 to direct radiation from X-ray source 306 (e.g., through a target) as the X-ray source rotates around the y-axis. Patient support (not shown) motion can be in an axial (longitudinal) direction along the y-axis, including as part of a scan as described above. Detector 302 also has a back (B) shadow region 312 and a front (F) shadow region 314 that are blocked from direct exposure to the radiation beam 308 by a beamformer/collimator 320. Beamformer/collimator 320 is configured to adjust a shape and/or position of the radiation beam 308 emitted by the x-ray source 306 onto detector 302. The shadowed regions 312, 314 will only receive scattered radiation.

The collimator 320 opening is configured in such a way that the back (B) end 312 and the front (F) end 314 of the detector 302 in the axial or longitudinal direction (along the patient table direction or y-axis) are not illuminated with direct radiation 308. These back (B) 312 (in the negative longitudinal direction along the rotation y-axis) and front (F) 314 (in the positive longitudinal direction along the rotation y-axis) shadow regions can be utilized for scatter measurement since they do not receive direct radiation. For example, a detector 302 readout range can be configured to read out all or a portion of the data in the one or more shadow regions 312, 314 and use the data for scatter estimation in the primary region 310. The primary or center (C) region 310 receives both direct projections and scatter.

A data processing system (e.g., processor 40) can be configured to receive measured projection data in the primary region 310 and measured scatter data in at least one shadow region 312, 314, then determine an estimated scatter in the primary region 310 based on the measured scatter data in at least one shadow region 312, 314. In some embodiments, determining the estimated scatter in the primary region 310 during a current rotation can be based on the measured scatter data in at least one shadow region 312, 314 during the neighboring (previous and/or subsequent) rotations. In other embodiments, measured data from penumbra region(s) (bordering the primary and shadow regions) may also be used for scatter estimation.

Some embodiments of collimator shadow fitting approaches can use a large amount of data from both sides of the collimator shadow regions 312, 314 for scatter fitting. Measuring a large amount of scatter data in the shadow regions 312, 314 can consume a lot of processing time and is not always required for reliable scatter fitting (estimating). For example, during a CBCT scan, a reduced detector readout range (including primary and read shadow regions) may be desirable to reduce the readout time, allowing scans with higher frame rates. However, when a reduced detector readout range is used and scatter estimation using collimator shadow data fitting is applied, a certain readout range still needs to be allocated to read out the data in the collimator shadow regions 312, 314. Hence, to reduce readout time, the effective detector area used for patient data acquisition in the primary region 310 would ordinarily be reduced in these embodiments, leading to reduced effective scanning field-of-view. Consequently, when a large axial range of the patient needs to be scanned, additional circular scans or helical scan rotations would be needed. Total scanning time would be increased and the treatment workflow and throughput will be adversely impacted.

However, in various embodiments described herein, use of asymmetric data fitting can be used for scatter estimation to alleviate the need to reduce the field-of-view (FOV). For example, some embodiments use a larger amount of data from one side of the collimator shadow and minimal data from the other side of the collimator shadow so that the total detector readout range used to readout data for scatter fitting is reduced, effectively increasing the scanning FOV when the limited detector readout range is used (or maintaining the scanning FOV when compared to a non-reduced detector readout range). This can be referred to as asymmetric scatter fitting.

FIGS. 4-7 show schematic views of exemplary detectors in scan designs with various shadow zones and detector readout ranges. The exemplary detectors are positioned to receive radiation from an x-ray source (not shown) emitting a radiation beam, wherein the detector includes a readout range. A beamformer (not shown) is configured to adjust a shape (e.g., width) and position (e.g., center) of the radiation beam emitted by the x-ray source, such that a primary region of the x-ray detector is directly exposed to the radiation beam and at least one shadow region of the x-ray detector is blocked from direct exposure to the radiation beam by the beamformer (e.g., as shown in FIG. 3).

For convenience, the following notation is used to identify the beam and detector regions in these figures along an axial direction (y-axis) of the x-ray imaging apparatus: let $L_D$ be the axial length of the detector with detector center $C_D$; let $L_A$ be the axial length of the aperture created by the beamformer with aperture center $C_A$; and let $L_R$ be the axial length of the detector readout (active) range with readout center $C_R$. Projecting the beam onto the detector creates primary region with axial length $L_C$ equal to $L_A$, back shadow region with axial length $L_{SB}$, and front shadow region with axial length $L_{SF}$. A back penumbra region with axial length $L_{PB}$ and front penumbra region with axial length $L_{PF}$ are between the primary and shadow regions. In this manner, the beamformer can be configured to project a radiation beam onto the detector such that $L_D = L_{SB} + L_{PB} + L_A + L_{PF} + L_{SF}$. Furthermore, the active readout area of the detector can be controlled/configured such that only a portion of the shadowed regions are read (active), where an active back shadow region has an axial length $L_B$ an active front shadow region has an axial length $L_F$.

Figure 4:
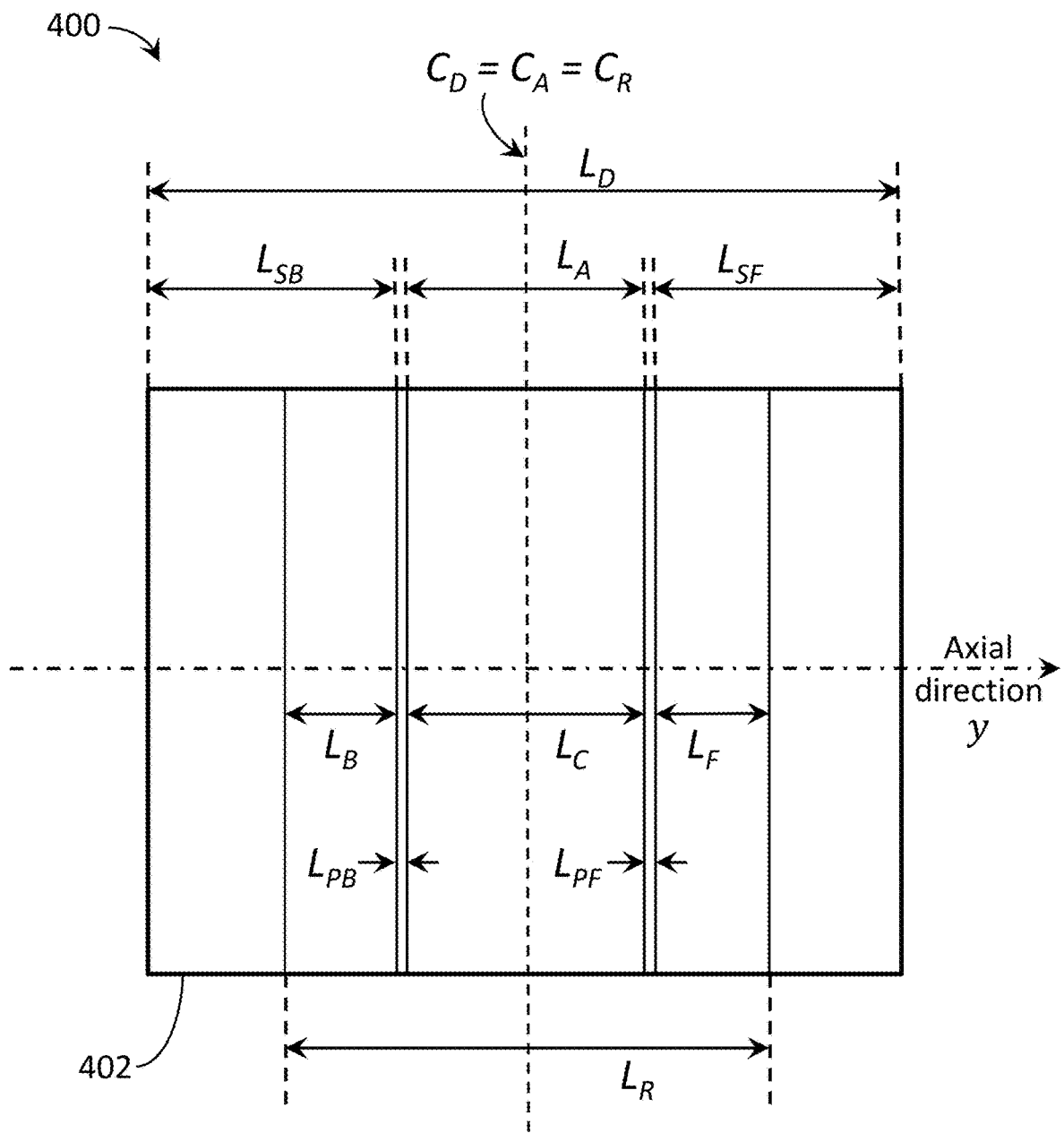
FIG. 4 is an illustration of an exemplary beam and detector configuration with symmetrical shadow readout regions.

FIG. 4 is an illustration of an exemplary beam and detector configuration 400 with symmetrical shadow readout regions. In this configuration, detector 402 is shown with the aperture center $C_A$ and the readout center $C_R$ aligned with the detector center $C_D$. Here, the active back shadow region $L_B$ and active front shadow region $L_F$ are equal in length and symmetrical on the detector 402.

As discussed above, to optimize readout time, scan speed, dosage, etc., various embodiments can utilize asymmetric shadow regions and their associated measurements, where a readout center $C_R$ of the readout range $L_R$ is offset from an aperture center $C_A$ of the primary region $L_C$ ($L_A$). This offset can be created by changing the shape (size/position) of the beam on the detector and/or by changing the size/position of the detector readout (active) area. To accommodate an optimized or reduced readout range $L_R$, FIGS. 5-7 show exemplary embodiments where a readout center $C_R$ of the readout range $L_R$ is offset from an aperture center $C_A$ of the primary region $L_C$, such that active (read) shadow regions $L_F$, $L_B$ are not equal, but are sufficient for scatter fitting and estimation.

Figure 5:
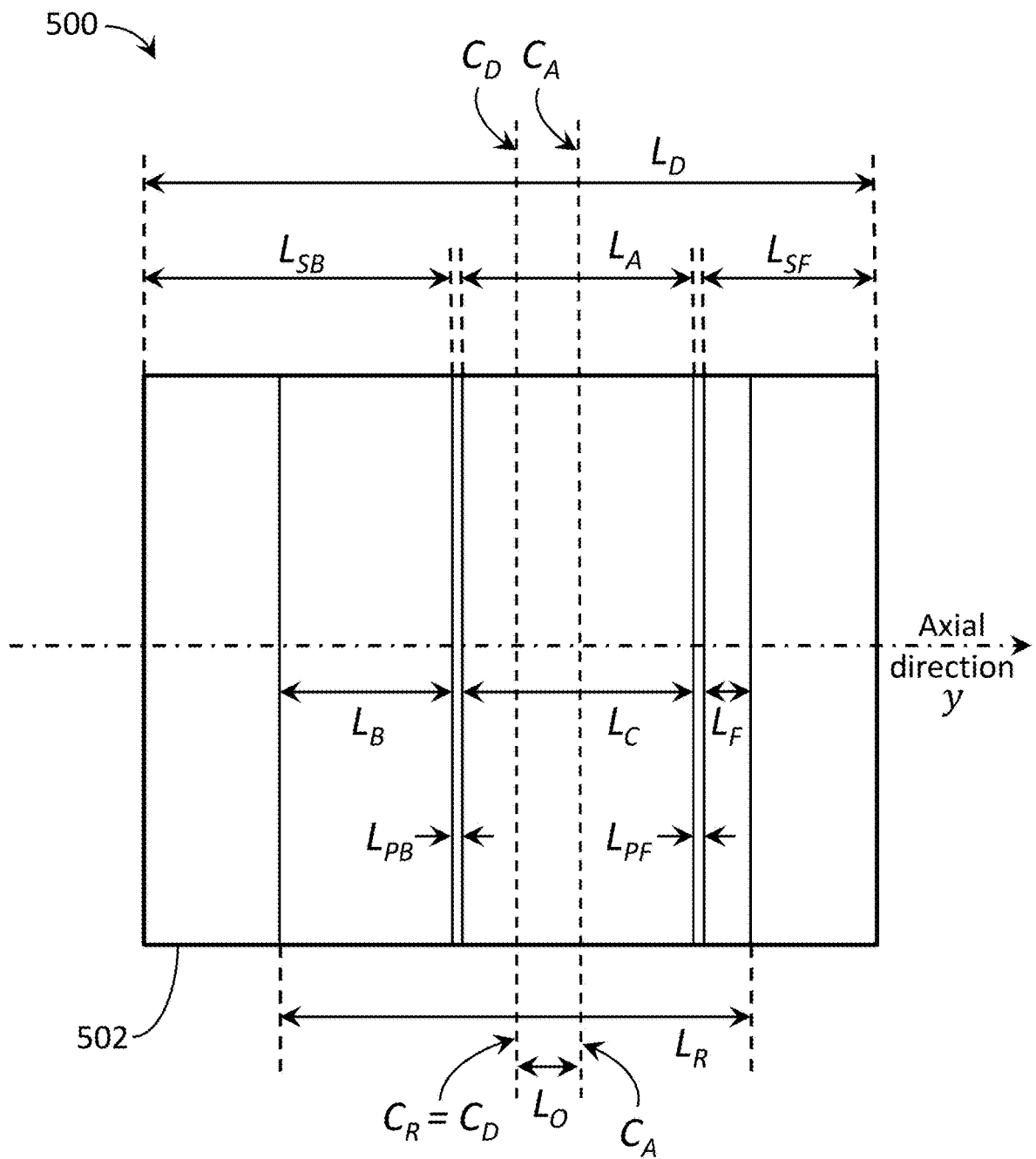
FIG. 5 is an illustration of an exemplary beam and detector configuration with asymmetrical shadow readout regions.

In one embodiment, FIG. 5 is an illustration of an exemplary beam and detector configuration 500 with asymmetrical shadow readout regions. In this embodiment, the readout range $L_R$ may be reduced but with the readout center $C_R$ aligned with the detector center $C_D$ of the detector 502. In this embodiment, the beamformer can adjust the shape of the of the radiation beam incident on the detector 502 so that the aperture center $C_A$ of the primary region $L_C$ is offset from the readout center $C_R$. The amount of offset is shown with an axial length $L_O$. In this configuration, the active back shadow region $L_B$ and active front shadow region $L_F$ become asymmetrical. Here, the active back shadow region $L_B$ is shown with an axial length greater than the active front shadow region $L_F$. In other embodiments, the aperture center $C_A$ can be offset in the opposite direction where $L_F$ is greater than $L_B$, with a similar effect. One or both shadow readout regions $L_F$, $L_B$ can be used for scatter fitting.

Figure 6:
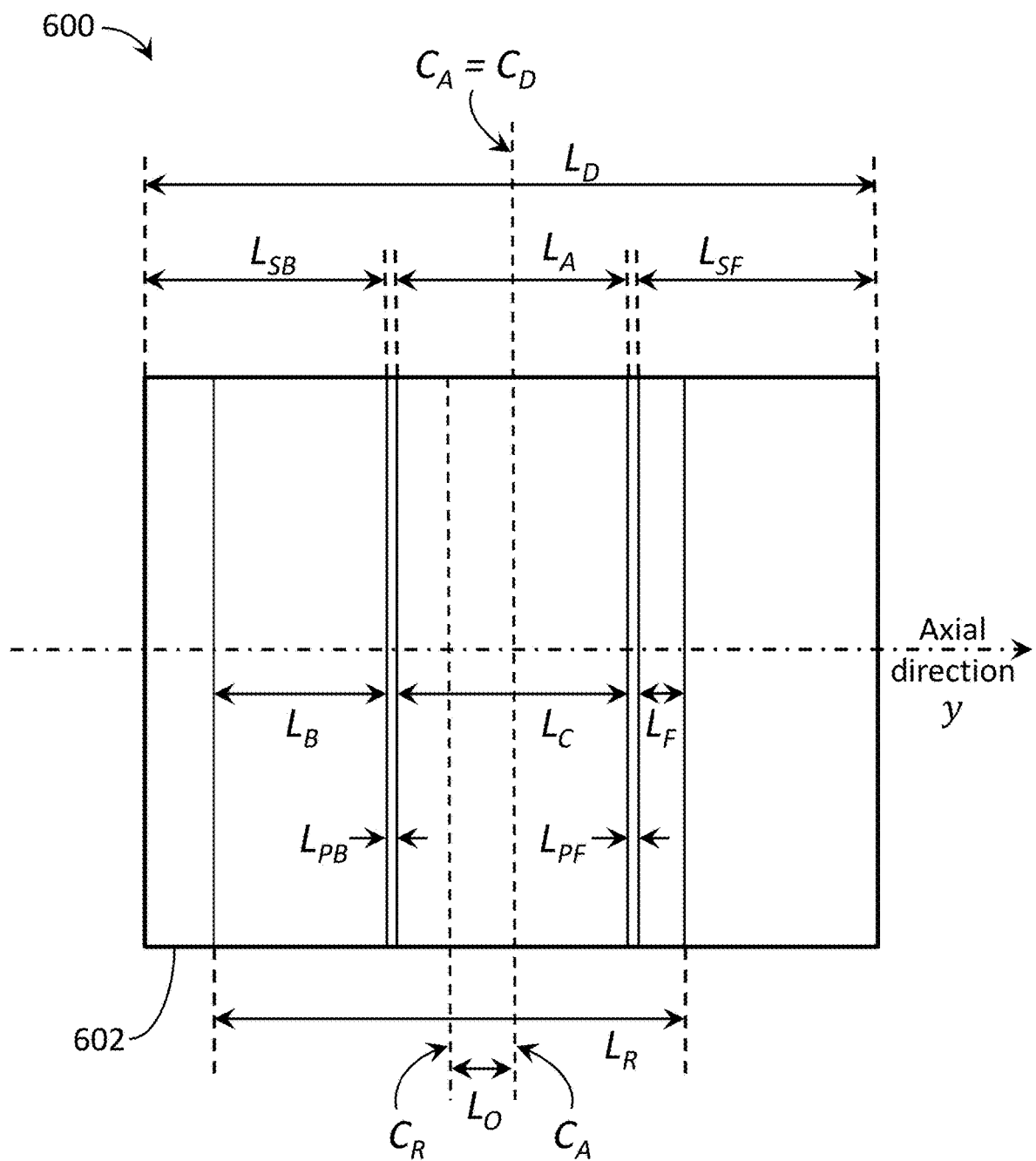
FIG. 6 is an illustration of another exemplary beam and detector configuration with asymmetrical shadow readout regions.

In another embodiment, FIG. 6 is an illustration of another exemplary beam and detector configuration 600 with asymmetrical shadow readout regions. In this embodiment, the readout range $L_R$ may be reduced with the readout center $C_R$ offset from the detector center $C_D$ of the detector 602. In this embodiment, the aperture center $C_A$ of the primary region $L_C$ is aligned with the detector center $C_D$. The amount of offset is shown with an axial length $L_O$. In this configuration, the active back shadow region $L_B$ and active front shadow region $L_F$ become asymmetrical. Here, the active back shadow region $L_B$ is shown with an axial length greater than the active front shadow region $L_F$. In other embodiments, the readout center $C_R$ can be offset in the opposite direction where $L_F$ is greater than $L_B$, with a similar effect. One or both shadow readout regions $L_F$, $L_B$ can be used for scatter fitting.

Figure 7:
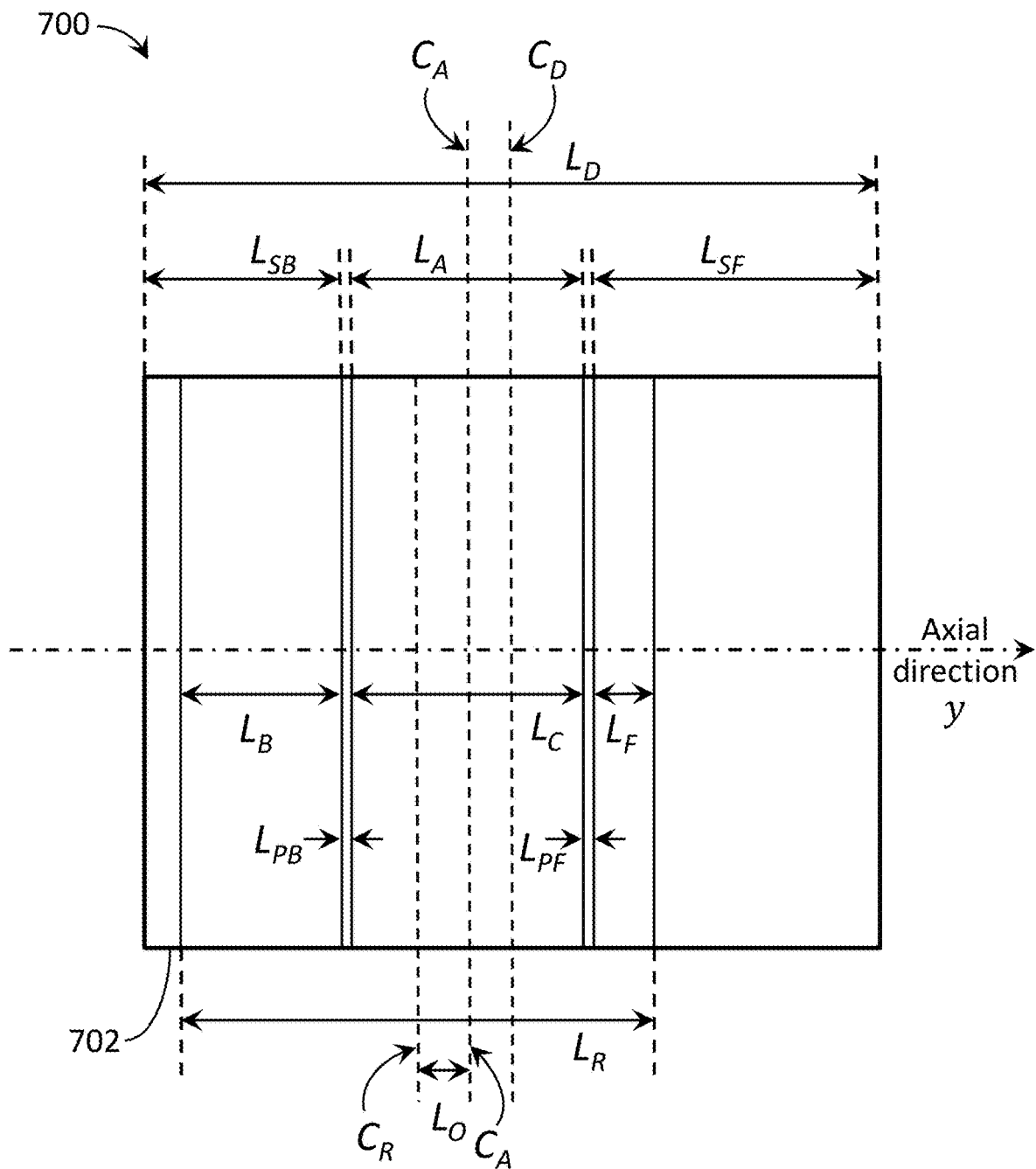
FIG. 7 is an illustration of another exemplary beam and detector configuration with asymmetrical shadow readout regions.

In another embodiment, FIG. 7 is an illustration of another exemplary beam and detector configuration 700 with asymmetrical shadow readout regions. In this embodiment, the readout range $L_R$ may be reduced with the readout center $C_R$ and the aperture center $C_A$ both offset from the detector center $C_D$ of the detector 702. The amount of the net offset between the readout center $C_R$ and the aperture center $C_A$ is shown with an axial length $L_O$. In this configuration, the active back shadow region $L_B$ and active front shadow region $L_F$ become asymmetrical. Here, the active back shadow region $L_B$ is shown with an axial length greater than the active front shadow region $L_F$. In other embodiments, the readout center $C_R$ and the aperture center $C_A$ can be offset in the opposite direction or with opposite respective offsets where $L_F$ is greater than $L_B$, with a similar effect. One or both shadow readout regions $L_F$, $L_B$ can be used for scatter fitting.

In any of these embodiments, an x-ray imaging apparatus (e.g., imaging apparatus 10) can include a data processing system (e.g., processor 40) configured to receive measured projection data in the primary region $L_C$ and measured scatter data in at least one shadow region $L_F$, $L_B$ and determine an estimated scatter in the primary region $L_C$ based on the measured scatter data in at least one shadow region $L_F$, $L_B$. In some embodiments, the data processing system may be configured to receive measured penumbra data in at least one penumbra region $L_{PF}$, $L_{PB}$ and determine the estimated scatter in the primary region $L_C$ based on the measured penumbra data in at least one penumbra region $L_{PF}$, $L_{PB}$.

The imaging design can include an optimization of the size of the primary region $L_C$ and the size of at least one shadow region $L_F$, $L_B$ within the readout range $L_R$, along with optimizing various other imaging considerations (including, for example, readout speed, scan speed, scatter estimation algorithms/protocols, machine constraints, etc.), resulting in an asymmetric shadow region configuration. As described above, in various embodiments, the desired size of the regions $L_C$, $L_F$, and/or $L_B$ can be implemented using a collimator (e.g., beamformer 36) with the ability to create variable beam widths on the detector, for example, via a device that can translate and/or rotate to adjust the aperture center r $C_A$ relative to the detector (e.g., x-ray detector 34) readout center $C_R$. In some embodiments, the desired size of the regions $L_C$, $L_F$, and/or $L_B$ can be implemented using detector readout control (e.g., sizing and positioning), via hardware and/or software, separately or in combination with the collimator.

Figure 8:
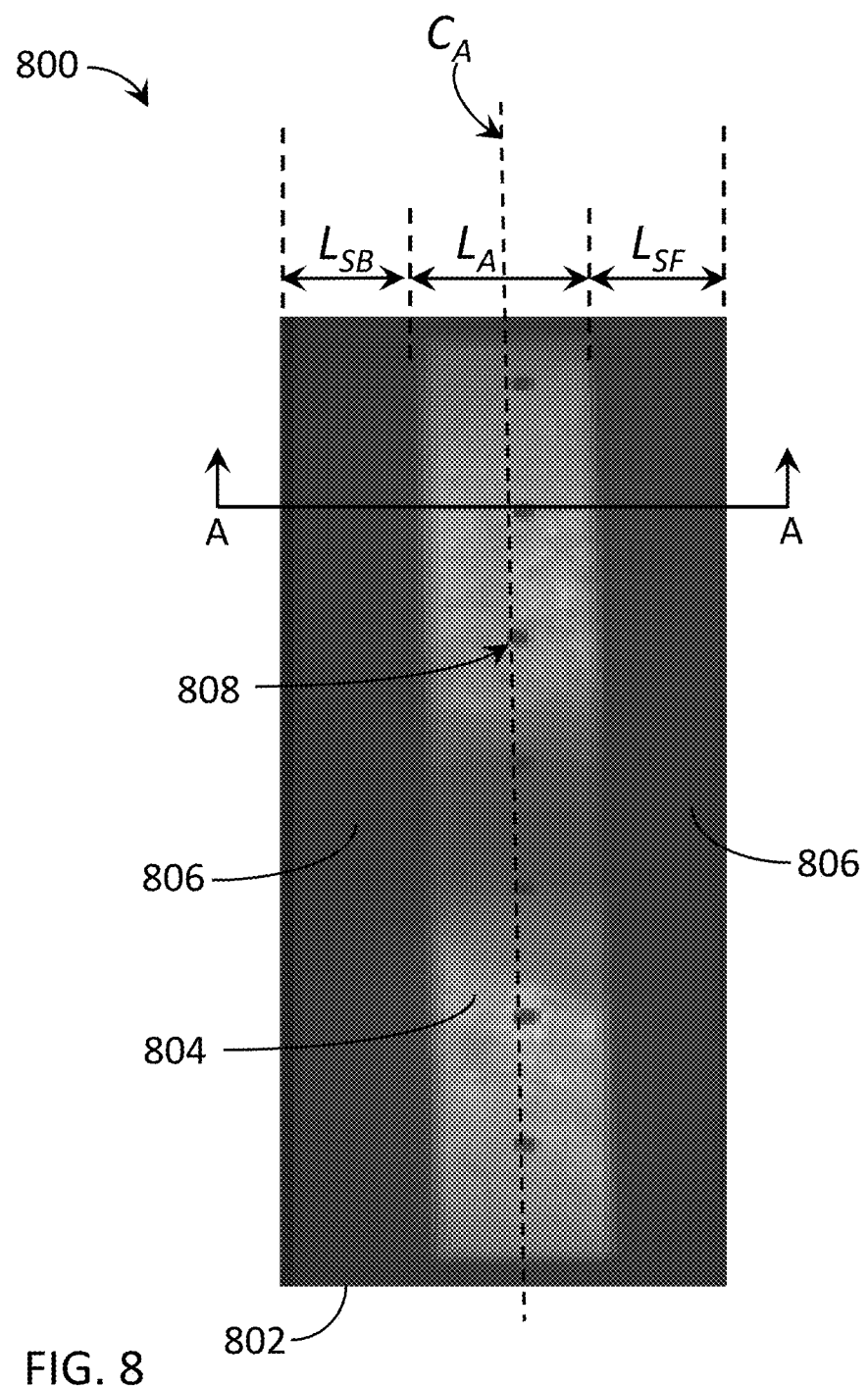
FIG. 8 is an illustration of an exemplary lung phantom projected onto a detector using an exemplary collimator opening.

For example, FIG. 8 is an illustration 800 of an exemplary lung phantom 804 projected onto a detector 802 using an exemplary narrow collimator opening. The center region is the lung phantom 804 exposed to the radiation beam and the black regions to the left and right are the collimator shadows 806. The black dots 808 are lead beads right before the phantom 804. In this configuration, detector 802 is shown with aperture center $C_A$. Projecting the beam aperture onto the detector creates a primary region with axial length $L_A$, a back shadow region with axial length $L_{SB}$, and a front shadow region with axial length $L_{SF}$.

Figure 9:
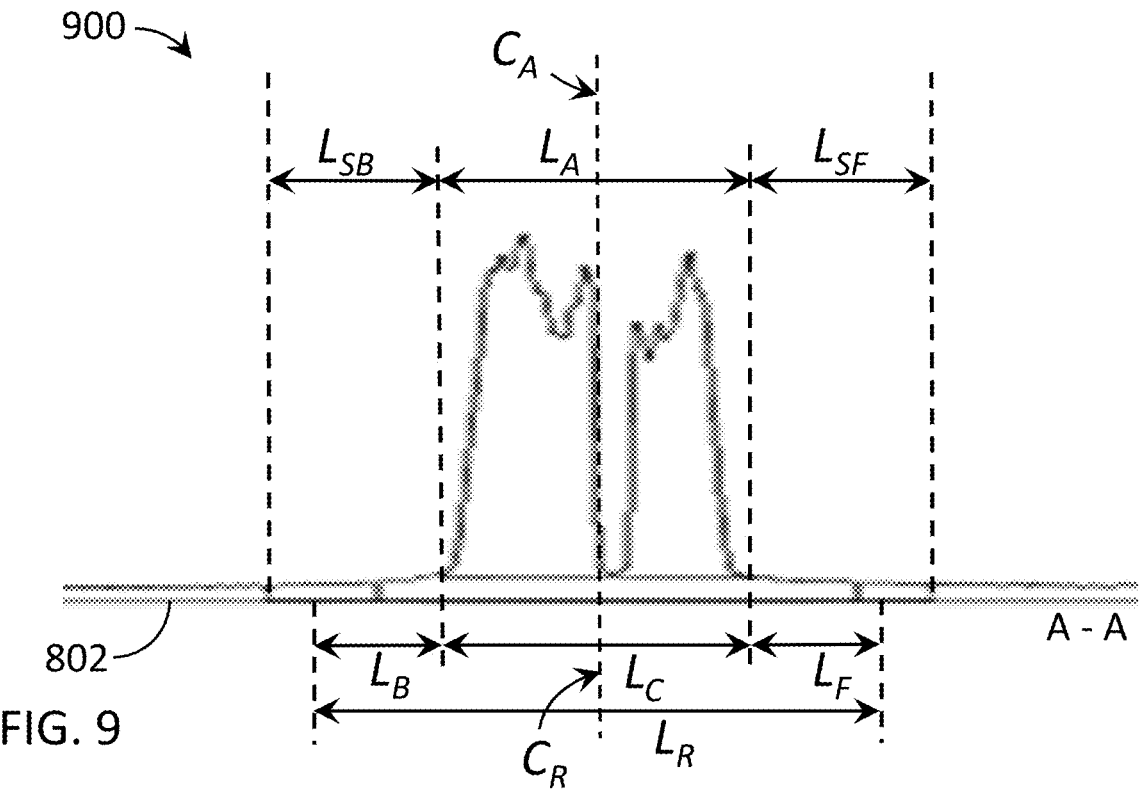
FIG. 9 is an illustration of an imaging design showing the data profile across the exemplary lung phantom shown in FIG. 8 with symmetrical shadow readout regions.
Figure 10:
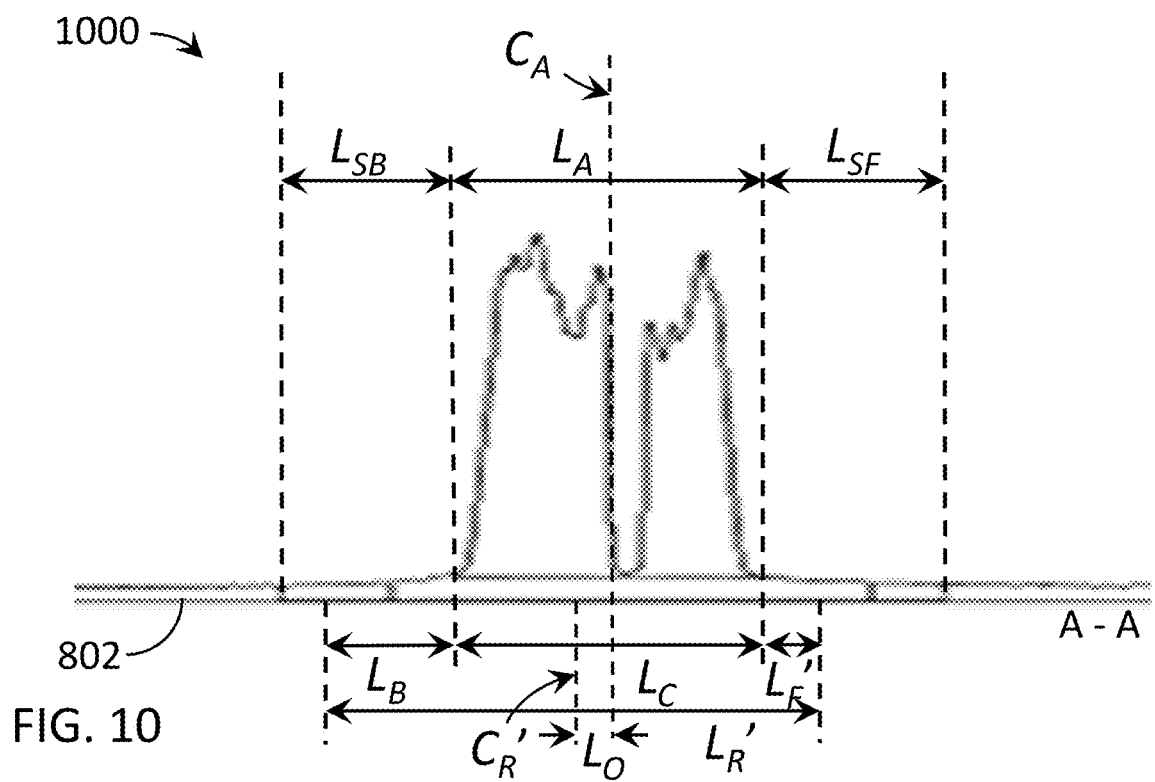
FIG. 10 is an illustration of an imaging design showing the data profile across the exemplary lung phantom shown in FIG. 8 with asymmetrical shadow readout regions.

FIGS. 9 and 10 illustrate imaging designs 900, 1000 with data profiles along the line A-A across the exemplary lung phantom 804 in the detector 802 plane shown in FIG. 8. The horizontal axis of the data profiles is the pixel position on the detector 802 plane. The vertical axis of the data profiles represents a plot of the measured data for each pixel along line A-A. The back shadow $L_{SB}$ range in the left side of the plot illustrates the range of data in the left collimator shadow area available for scatter estimation (fitting). The front shadow $L_{SF}$ range in the right of the plot illustrates the range of data in the right collimator shadow area available for scatter estimation. The detector 802 potential readout range $L_R$ is shown with a readout center $C_R$. Data outside of the readout range $L_R$ of the detector 802 will not be read and thus not available for use. With a limited detector readout range, the data that can be used for scatter fitting has to be reduced if the collimator opening is kept the same.

FIG. 9 is an illustration of an imaging design 900 with the data profile along line A-A across the exemplary lung phantom 804 in the detector 802 plane shown in FIG. 8 with symmetrical shadow readout regions. In this configuration, detector 802 is shown with the aperture center $C_A$ aligned with the readout center $C_R$. Here, the readout range $L_R$ of the detector 802 is shown with the primary region having an axial length $L_C$. The active back shadow region $L_B$ and active front shadow region $L_F$ are equal in length and symmetrical on the detector 802. In this embodiment, $L_B$ and $L_F$ are representative of typical shadow region sizes necessary for sufficient scatter estimation.

However, as discussed above, for example, to reduce readout time, various embodiments include a reduced readout range $L_R$ of the detector 802 and can utilize asymmetric shadow regions, where a readout center $C_R$ of the readout range $L_R$ is offset from an aperture center $C_A$ of the primary region $L_C$ ($L_A$). For example, FIG. 10 is an illustration of an imaging design 1000 with the data profile along line A-A across the exemplary lung phantom 804 in the detector 802 plane shown in FIG. 8 with asymmetrical shadow readout regions. Here, the readout range $L_R'$ of the detector 802 is reduced relative to the readout range $L_R$ shown in FIG. 9, but the primary region axial length $L_C$ (FOV) is maintained. The axial length of the active back shadow region $L_B$ is also maintained for scatter estimation. To accommodate the reduced readout range $L_R'$ and the same primary region $L_C$, the active front shadow region $L_F'$ is reduced when compared to the active front shadow region $L_F$ of FIG. 9. Consequently, the readout center $C_R'$ is offset from the aperture center $C_A$ (and the readout center $C_R$ of FIG. 9) by $L_O$. In this embodiment, the active back shadow region $L_B$ and active front shadow region $L_F'$ are not equal in length (asymmetrical), but are sufficient for scatter fitting and estimation.

In various embodiments, the offset Lo between the aperture center $C_A$ and the readout center $C_R$ can be created by changing the shape (size/position) of the beam on the detector (e.g., by shifting the aperture center $C_A$ of the beam on the detector) and/or by changing the size/position of the detector readout (active) area $L_R$, as described above.

Figure 11:
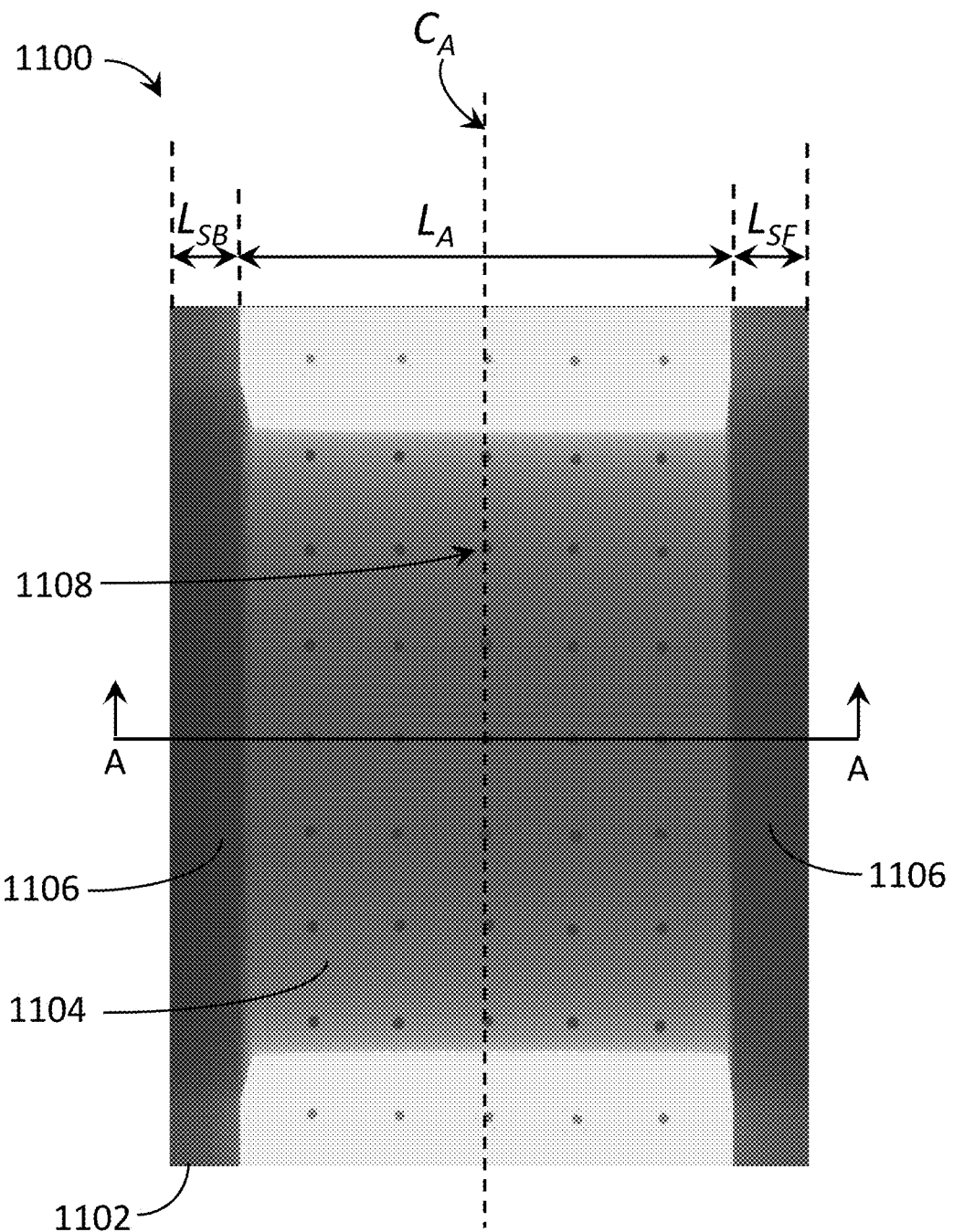
FIG. 11 is an illustration of an exemplary lung phantom projected onto a detector using an exemplary collimator opening.

In another example, FIG. 11 is an illustration 1100 of an exemplary lung phantom 1104 projected onto a detector 1102 using an exemplary collimator opening. The center region is the lung phantom 1104 exposed to the radiation beam and the black regions to the left and right are the collimator shadows 1106. The black dots 1108 are lead beads right before the phantom 1104. In this configuration, detector 1102 is shown with aperture center $C_A$. Projecting the beam aperture onto the detector creates a primary region with axial length $L_A$, a back shadow region with axial length $L_{SB}$, and a front shadow region with axial length $L_{SF}$. The back shadow $L_{SB}$ range and the front shadow $L_{SF}$ range illustrate the range of data in the collimator shadows available for scatter estimation.

Figure 12:
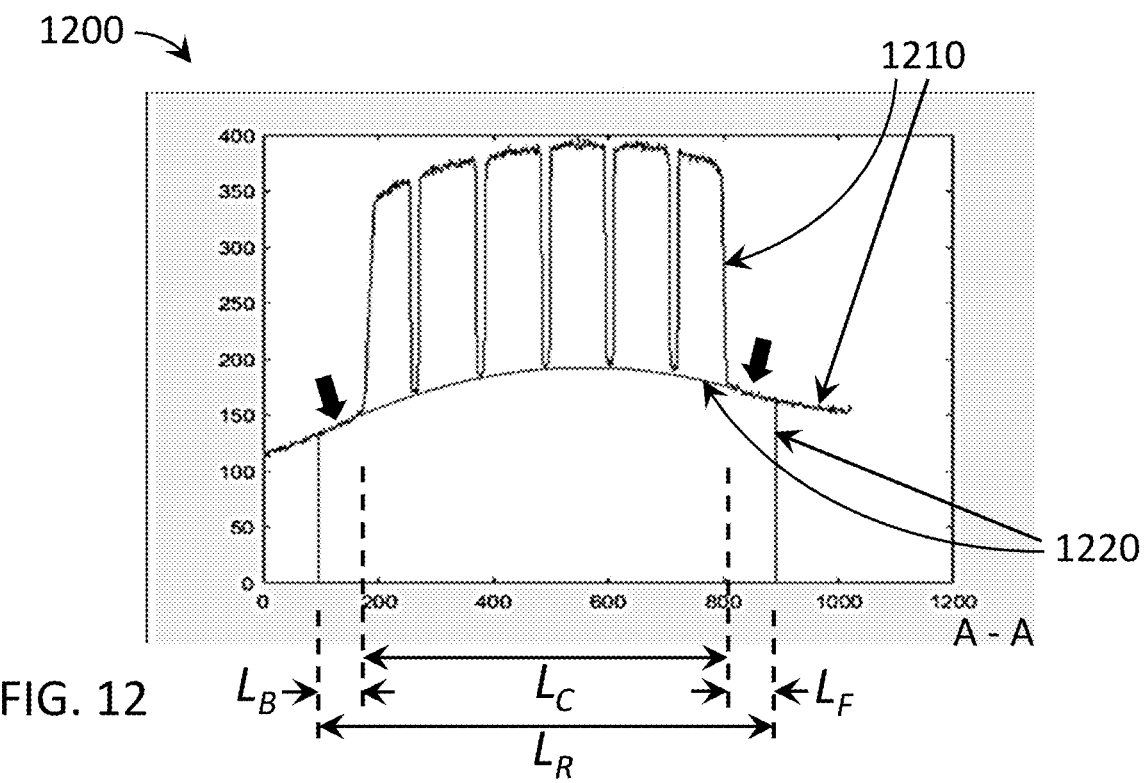
FIG. 12 is a data plot across the exemplary lung phantom shown in FIG. 11 with symmetrical shadow readout regions.
Figure 13:
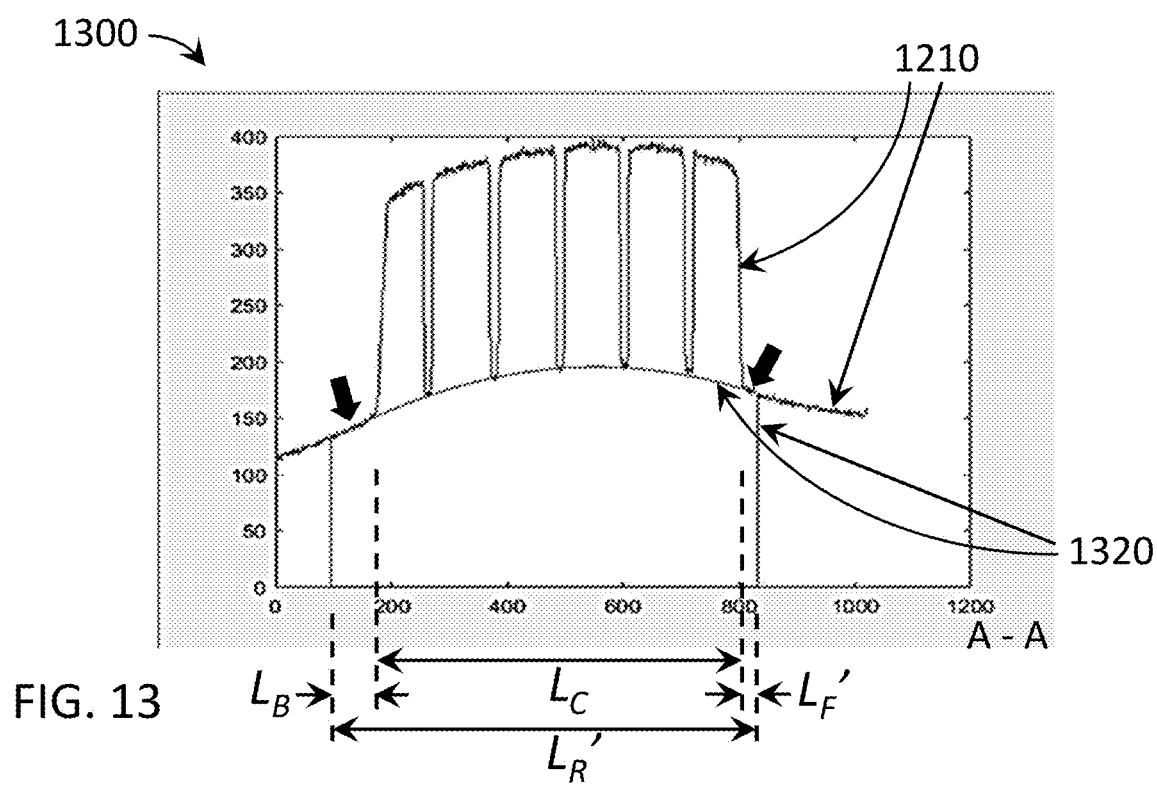
FIG. 13 is a data plot across the exemplary lung phantom shown in FIG. 11 with asymmetrical shadow readout regions.

FIGS. 12 and 13 illustrate symmetric scatter fitting and asymmetric scatter fitting, respectively, with experimental data showing the effectiveness of the disclosed asymmetric scatter fitting applied to a data profile along the line A-A across the exemplary lung phantom 1104 in the detector 1102 plane shown in FIG. 11. The horizontal axis of the data profiles is the pixel position on the detector 1102 plane and the vertical axis of the data profiles represents a plot of the measured data for each pixel along line A-A.

FIG. 12 is a data plot 1200 along line A-A across the exemplary lung phantom 1104 in the detector 1102 plane shown in FIG. 11 with symmetrical shadow readout regions. Here, the readout range $L_R$ of the detector 1102 is shown with the primary region having an axial length $L_C$ and where the active back shadow region $L_B$ and active front shadow region $L_F$ are equal in length and symmetrical. In this embodiment, $L_B$ and $L_F$ are representative of typical shadow region sizes used for sufficient scatter estimation.

FIG. 13 is a data plot 1300 along line A-A across the exemplary lung phantom 1104 in the detector 1102 plane shown in FIG. 11 with asymmetrical shadow readout regions. Here, the readout range $L_R'$ of the detector 1102 is reduced relative to the readout range $L_R$ shown in FIG. 12, but the primary region axial length $L_C$ (FOV) is maintained. The axial length of the active back shadow region $L_B$ is also maintained for scatter estimation. To accommodate the reduced readout range $L_R'$ and the same primary region $L_C$, the active front shadow region $L_F'$ is reduced when compared to the active front shadow region $L_F$ of FIG. 12.

Measured data line 1210 is the line profile along line A-A across the illuminated region on the detector 1102 extended into the collimator shadows $L_{SB}$, $L_{SF}$ of the lung phantom 1104. The tails on the ends of the measured data line 1210 are in the collimator shadows $L_{SB}$, $L_{SF}$. The dips in measured data line 1210 are the small shadowed areas where the x-ray is blocked by the lead bead array 1108 right before the phantom 1104.

Scatter lines 1220, 1320 are the fitted (estimated) scatter in FIGS. 12 and 13, respectively. The overlapping portion of the measured data line 1210 and the scatter lines 1220, 1320 (identified in the figures by the block arrows) indicates the data from the collimator shadows $L_B$ and $L_F$, $L_F'$ that are used for scatter fitting. The measured data 1210 in the lead bead 1108 shadows are used as a reference for the fitted scatter (after being offset by lead bead 1108 penetration). As shown by the experimental data in FIGS. 12 and 13, scatter lines 1220, 1320 both touch the dips of the lead bead 1108 shadows in the plots 1200, 1300. This evidence confirms the effectiveness of the asymmetric scatter fitting/estimate 1320 when compared to a symmetric scatter fitting/estimate 1220 applied to the same measured data 1210.

In various embodiments, the offset between the aperture center and the readout center can be created by changing the shape (size/position) of the beam on the detector (e.g., by shifting the aperture center of the beam) and/or by changing the size/position of the detector readout (active) area, as described above.

Although not shown in FIGS. 10 and 13, penumbra regions (bordering the primary and shadow regions, e.g., as shown in FIGS. 4-7 as $L_{PB}$ and $L_{PF}$) may be utilized in various embodiments. In an asymmetrical implementation, if the two sides of the collimator have systematically different penumbra, then the side with the larger penumbra width may be more suitable for the reduced shadow region (e.g., $L_F'$ as shown in FIGS. 10 and 13).

In an extreme implementation of the asymmetric scatter fitting, only the collimator shadow from one side is read and no detector area is used to read the collimator shadow from the other side. Generally, scatter fitting does not work when there is only data from a collimator shadow on one side. In this embodiment, an imaging design implements dual scans in which the detector readout range is cut off at the penumbra of the collimator on one side during a first scan and is cut off at the penumbra of the collimator's other side during a second scan. The first scan includes collimator shadow data available from one side and the second scan includes collimator shadow data available from the other side.

For example, in one embodiment, a second scan can include a shift in the collimator opening relative to the detector readout region, so that the collimator shadow on the other side is read. In these embodiments, by combining the collimator shadow data from one side in the first scan and the collimator shadow data from the other side in the second scan, sufficient collimator shadow data is obtained and available for scatter estimation. This design allows the detector readout range to cut off at the penumbra range at one side of the collimation during each scan, maximizing the useful scanning FOV. Combining the available data can provide a scatter estimation as reliable as conventional collimator shadow fitting approaches.

Figure 14:
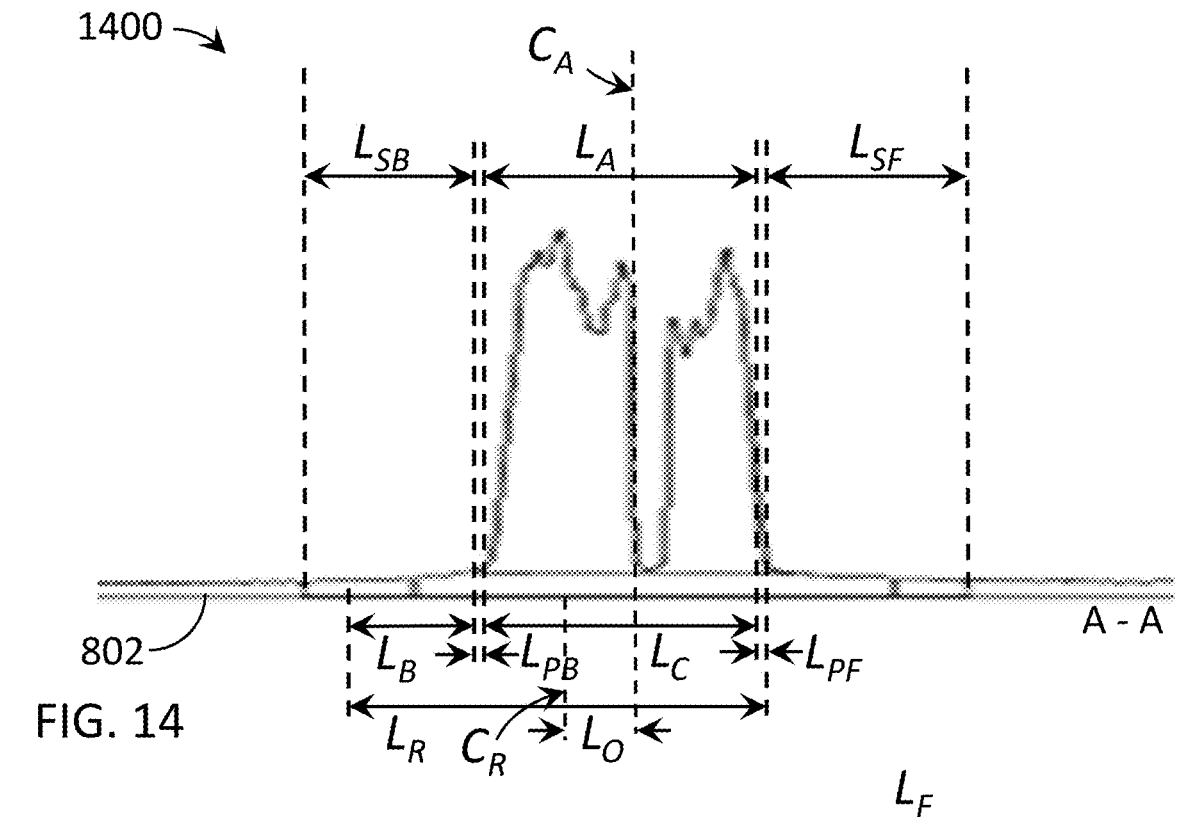
FIG. 14 is an illustration of an imaging design showing the data profile across the exemplary lung phantom shown in FIG. 8 in the first scan of a dual scan.
Figure 15:
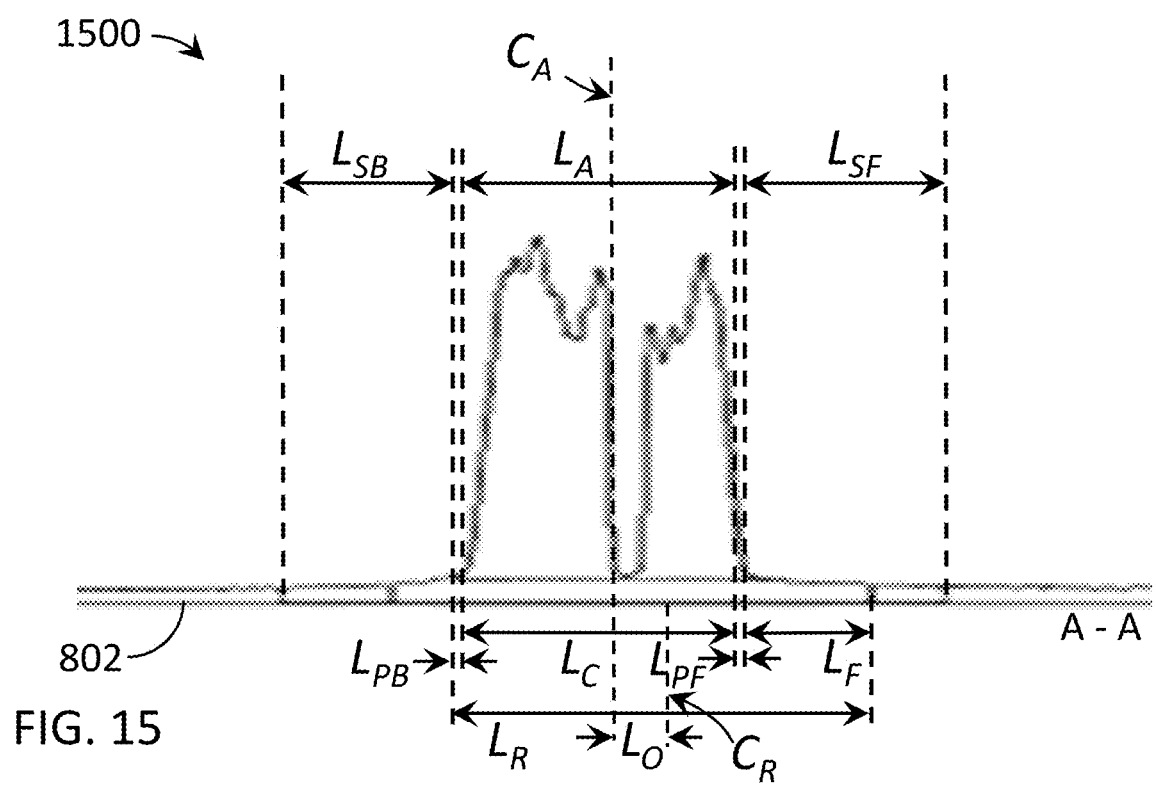
FIG. 15 is an illustration of an imaging design showing the data profile across the exemplary lung phantom shown in FIG. 8 in the second scan of a dual scan.

For example, FIGS. 14 and 15 illustrate imaging designs 1400, 1500 with data profiles along the line A-A across the exemplary lung phantom 804 in the detector 802 plane shown in FIG. 8. As mentioned above, the back shadow LSB range in the left side of the plot illustrates the range of data in the left collimator shadow area available for scatter estimation (fitting). The front shadow $L_{SF}$ range in the right of the plot illustrates the range of data in the right collimator shadow area available for scatter estimation. A reduced readout range $L_R$ of the detector 802 is shown with readout center $C_R$ offset from the aperture center $C_A$ by an offset $L_O$.

FIG. 14 is an illustration of an imaging design 1400 with the data profile along line A-A across the exemplary lung phantom 804 serving as the first scan of a dual scan, with asymmetrical shadow readout regions. In this design 1400, the readout range $L_R = L_B(+L_{PB}) + L_C(+L_{PF})$, where $L_{PB}$ and $L_{PF}$ are the penumbra regions, which may be used in certain embodiments, as discussed below. In this manner, only one shadow region $L_B$ is read for scatter estimation data (along with primary region $L_C$ in the readout range $L_R$). FIG. 15 is an illustration of an imaging design 1500 with the data profile along line A-A across the exemplary lung phantom 804 serving as the second scan of the dual scan, with asymmetrical shadow readout regions. In this design 1500, the readout range $L_R = (L_{PB}+) L_C (+L_{PF}) + L_F$. In this manner, only the opposite shadow region $L_F$ is read for scatter estimation data.

In one embodiment, shifting the collimator aperture center $C_A$ relative to the readout center $C_R$ of the detector readout range $L_R$ can maximize (optimize) the effective data acquisition area on the detector in a dual-scan approach. In the first scan (e.g., as shown in FIG. 14), the left collimator shadow area $L_B$ overlaps with the detector readout range $L_R$ and provides left data for scatter fitting, yet the detector readout range $L_R$ aligns with (cuts off at) the right penumbra $L_{PF}$ (since the penumbra area has contaminated, and at least lower statistics data for CT reconstruction). In the second scan (e.g., as shown in FIG. 15), the collimator (and its aperture center $C_A$) is adjusted (e.g., shifted) relative to the detector and its readout range $L_R$. The detector readout range $L_R$ aligns with (cuts off at) the left penumbra $L_{PB}$ and overlaps with the right collimator shadow $L_F$ to provide sufficient data for scatter fitting. By combining the data from the left and the right shadow regions, sufficient scatter data from both the left and the right of the primary region is available for accurate scatter fitting.

In this dual design embodiment, if the first scan and the second scan use different doses (e.g., mA), then the collimator shadow data from the two scans can be scaled or weighted accordingly prior to or during the scatter fitting and/or reconstruction process. Furthermore, measured projection data in the primary region can be reconstructed separately for each scan, using the estimated scatter with scaling/weighting related to the dose of each scan. Also, in some embodiments, the data from the two scans can be reconstructed jointly, for example, by joining the data prior to reconstruction or during reconstruction, while the estimated scatter is used for scatter correction accordingly.

In one embodiment, determining the estimated scatter in the measured projection data comprises scaling the measured scatter data in at least one shadow region based on a difference between the doses during the scans. In another embodiment, determining the estimated scatter in the measured projection data comprises scaling the measured projection data from the first scan or the second scan based on a difference between the doses during the scans.

Penumbra regions associated with a collimator (e.g., $L_{PB}$ and $L_{PF}$) are generally not used in conventional CT or CBCT scans. Typically, a penumbra region at each side of the beam collimator covers a detector range that is usually about the size of the focal point of the source multiplied by the amplification factor. To make the scatter estimation more accurate, the penumbra region of the collimator/beamformer can be excluded. In one embodiment, this can be achieved by automatically detecting the axial profile of each projection and then excluding a number of predefined pixels in the axial direction. Another method is to perform an experiment ahead of time for different window and scan configurations and predefine the back and front regions for scatter measurement in view of the penumbra area.

However, in some embodiments, the asymmetrical scatter estimation technique can estimate the scatter in the penumbra region (e.g., $L_{PB}$ and/or $L_{PF}$) and use the obtained scatter for scatter estimation in the primary region $L_C$ corresponding to the collimator aperture $L_A$. These embodiments reduce the required data needed in the collimator shadow region (e.g., $L_B$ and/or $L_F$) for accurate scatter fitting/modeling, and consequently enable increased effective scanning FOV ($L_C$) for a given detector readout range $L_R$. In one embodiment, the collimator side with the smaller shadow region readout is the side with a larger penumbra.

In this manner, the scatter measured in the penumbra region(s) (e.g., $L_{PB}$ and/or $L_{PF}$) can be modeled and used as data for scatter estimation in the primary region (e.g., $L_C$) corresponding to the collimator opening. This can reduce the amount of data required in the collimator shadow region (beyond the penumbra) for scatter fitting, allowing more area in the detector readout range $L_R$ to be used for the primary region $L_C$ (FOV for patient scan data).

For example, if the penumbra in air can be accurately measured and mapped ($P_{map}$), then the scatter in the penumbra can be estimated. In one embodiment, a first reconstruction of the image is performed without scatter correction. An estimated projection to the penumbra area is computed (Pp) and an estimated projection of the pixels next to the penumbra into the opening (Po) is also computed. The measured projection data in the pixels next to the penumbra into the opening (PoM) is scaled and modulated by the penumbra map (PM) to estimate the following value that is the modulated primary (P_primary) in the penumbra and the scatter in the PoM (Po_scatter), where:

$$\left[PoM * \left(\frac{Pp}{Po}\right)\right] \otimes P_{map} = \text{P\_primary} \otimes P_{map} + \text{Po\_scatter} \otimes P_{map} \qquad (1)$$

Here, $\oplus$ stands for the modulation, which, for example, can be a simple pixel-wise multiplication. The measured values in the penumbra are:

$$PM = \text{P\_primary} \oplus P_{map} + \text{P\_scatter} \qquad (2)$$

Assuming that the scatter in penumbra area and the pixels next to the penumbra into the opening are the same, then the following relationship between the scatter in the penumbra and the measured penumbra values and the value of the pixels next to the penumbra into the collimator opening:

$$\text{P\_scater} = \text{P\_scatter} \otimes P_{map} = PM - \left[PoM * \left(\frac{Pp}{Po}\right)\right] \otimes P_{map} \qquad (3)$$

If using a simple pixelwise multiplication for the penumbra modulation, then the scatter in the penumbra is:

$$P_{scatter} = \frac{PM - \left[PoM * \left(\frac{Pp}{Po}\right) * P_{map}\right]}{1 - P_{map}} \quad (4)$$

In one embodiment, an iterative approach can be applied to improve the accuracy of the above technique. For example, the process above can be performed after the first scatter correction using scatter fitted from the scatter measured in the collimator shadow and the scatter estimated from the penumbra. This can result in a more accurate estimation of the scatter in the penumbra, which in turn enables a more accurate scatter estimation.

In another embodiment, the scatter fitting using the obtained scatter in penumbra can have a different weight for the data from the collimator shadow and the data from the penumbra.

Various techniques and methods can utilize different scan geometries, detector positioning, and/or beamformer window shapes. In some embodiments, the detector may also be offset in the transverse direction.

The following flow charts and block diagrams illustrate exemplary configurations and methodologies associated with scatter estimation in accordance with the systems described above. The exemplary methodologies may be carried out in logic, software, hardware, or combinations thereof. In addition, although the procedures and methods are presented in an order, the blocks may be performed in different orders, including series and/or parallel. Thus, the steps below, including imaging, image-based pre-delivery steps, and treatment delivery, although shown sequentially, may be executed simultaneously, including in real-time. Further, additional steps or fewer steps may be used.

Figure 16:
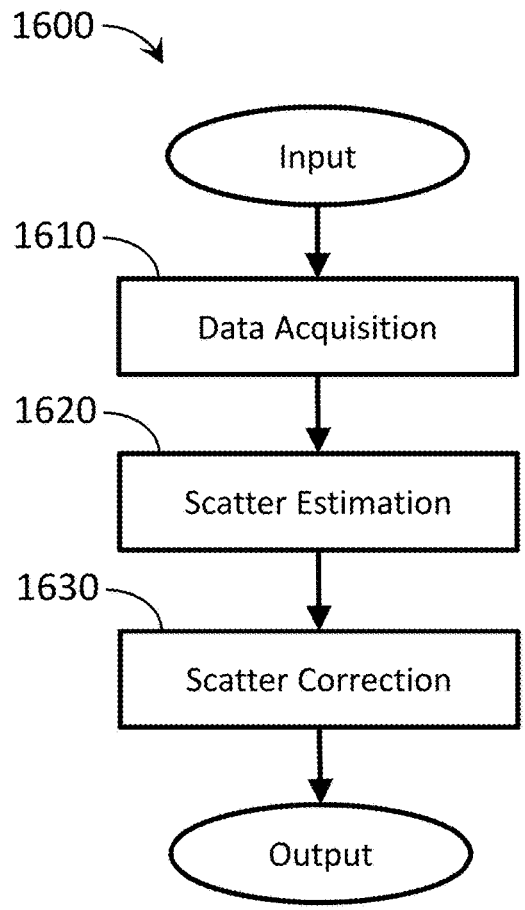
FIG. 16 is a flow chart depicting an exemplary method of scatter correction.

FIG. 16 is a flow chart depicting an exemplary method 1600 of scatter estimation and correction using an asymmetric scan design, such as those described above. Inputs can include any optional prior data and/or scan designs. In this embodiment, step 1610 includes data acquisition. For example, during rotation of a radiation source projecting a collimated radiation beam towards a target and radiation detector, the method measures projection data (primary+scatter) in a central (primary) region of a radiation detector and measures scatter using a front shadow peripheral region and/or a back shadow peripheral region of the detector. In these embodiments, an aperture center of the primary region is offset from a readout center of the readout range during the scan, such that the front and back shadow regions are asymmetrical (including where only one shadow region is used), in accordance with any of the embodiments described above.

Data acquisition in step 1610 can also include adjusting a shape/position of the radiation beam with the beamformer before and/or during the scan. Adjusting the radiation beam with the beamformer can include rotation and translation of highly x-ray attenuated material of the beamformer during the scan to block radiation from directly exposing shadow regions. Step 1610 can also include adjusting a readout range (including shifting the active region). Adjusting the radiation beam and/or readout range can be used to create the asymmetric shadow regions by offsetting the aperture center of the primary region and the readout center of the x-ray detector.

Next, step 1620 includes scatter estimation. For example, the method estimates the scatter in the projection data from the central (primary) region using the scatter measurement from the shadow region(s) and/or penumbra region(s), in accordance with any of the embodiments described above. Then, step 1630 includes scatter correction. For example, scatter estimated from step 1620 is subtracted from the projection data to obtain scatter corrected projection data. Output includes scatter corrected projection data suitable for imaging. Various embodiments can utilize different scan geometries, detector positioning/active areas, beamformer positioning/window shapes, etc.

Figure 17:
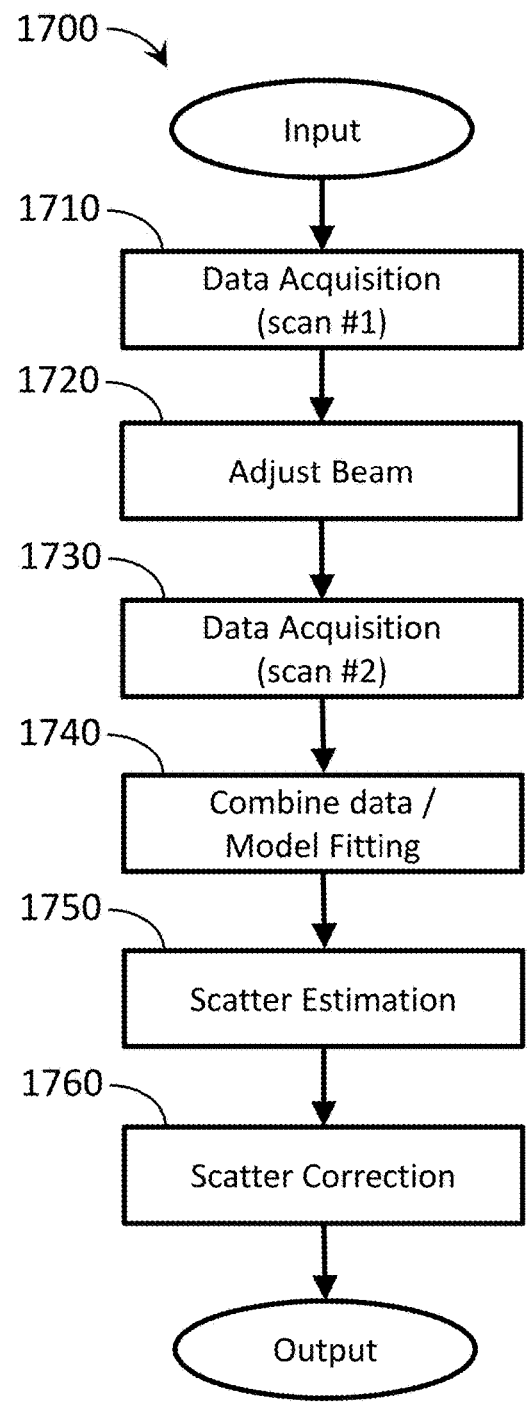
FIG. 17 is a flow chart depicting another exemplary method of scatter correction.

FIG. 17 is a flow chart depicting an exemplary method 1700 of scatter estimation and correction using an asymmetric scan design with a first and second scan, such as those described above. Inputs can include any optional prior data and/or scan designs. In this embodiment, step 1710 includes data acquisition during the first scan, where the method measures projection data in a central (primary) region of a radiation detector and measures scatter in a first shadow region of the detector. Next, at step 1720, the method adjusts a position of the radiation beam between the first scan and the second scan. For example, step 1720 can adjust the beam such that the first shadow region overlaps with a first side of a detector readout range during the first scan and a second shadow region overlaps with a second side of the readout range during the second scan. Then, step 1730 includes data acquisition during the second scan, where the method measures projection data in a central (primary) region of the radiation detector and measures scatter in the second shadow region of the detector. Then, at step 1740, the method can combine the measured scatter data from the first and second shadow regions, including with use of various model fitting techniques. In some embodiments, step 1740 may be skipped or combined with step 1750.

Next, step 1750 includes scatter estimation, where the method estimates the scatter in the projection data from the central (primary) region using the scatter measurements from the first and second shadow regions. Then, step 1760 includes scatter correction, where the method subtracts the estimated scatter from the projection data to obtain scatter corrected projection data. Output includes scatter corrected projection data suitable for imaging. Like the steps of method 1600, steps of method 1700 can be implemented in accordance with any of the embodiments described above.

Figure 18:
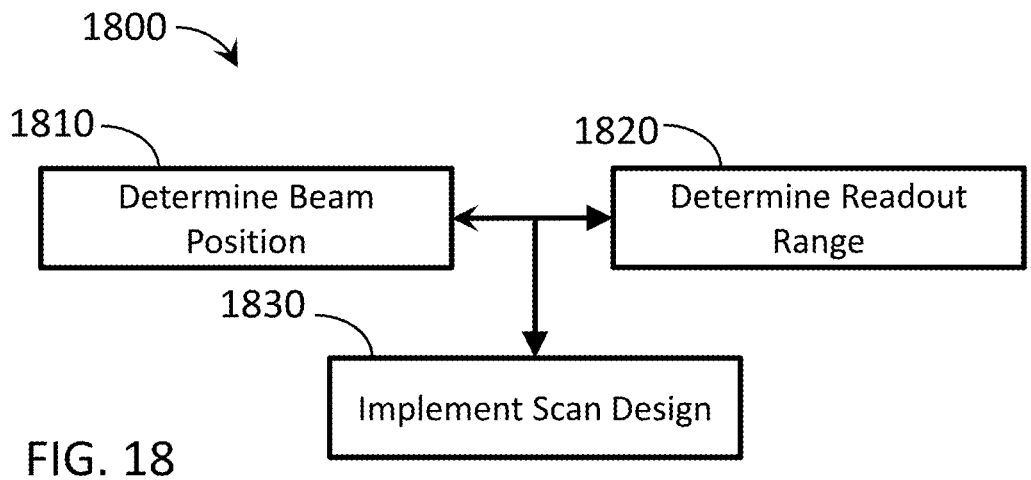
FIG. 18 is a flow chart depicting an exemplary method of optimizing an asymmetric scan design.

One or more optimization processes are also applicable to all of the above embodiments to determine beam positioning, determine readout range, estimate scatter, etc. For example, in one embodiment, FIG. 18 is a flow chart depicting an exemplary method 1800 of optimizing an asymmetric scan design, such as those described above. One constraint and/or goal during optimization may be a target or reduced readout time. As discussed above, reducing the detector readout range (including primary and read shadow regions) can reduce the readout time, allowing scans with higher frame rates. However, when a reduced detector reading range is used and scatter estimation using collimator shadow data fitting is applied, a minimum or target readout range may need to be allocated to read out the data in the collimator shadow regions. Total scanning time, treatment workflow, and/or throughput can be additional factors. Step 1810 includes determining beam positioning. Step 1820 includes determining a detector readout range. In some embodiments, step 1810 or 1820 may be optional, limiting the optimization to the other variable. In other embodiments, steps 1810 and 1820 may be executed in a certain order, simultaneously, and/or iteratively. For example, one step may be executed to reach an initial optimized design, and then the other step may be executed in view of the other, and vice versa, including iteratively, to optimize the design. Then at step 1830, the scan design can be implemented as described above.

Figure 19:
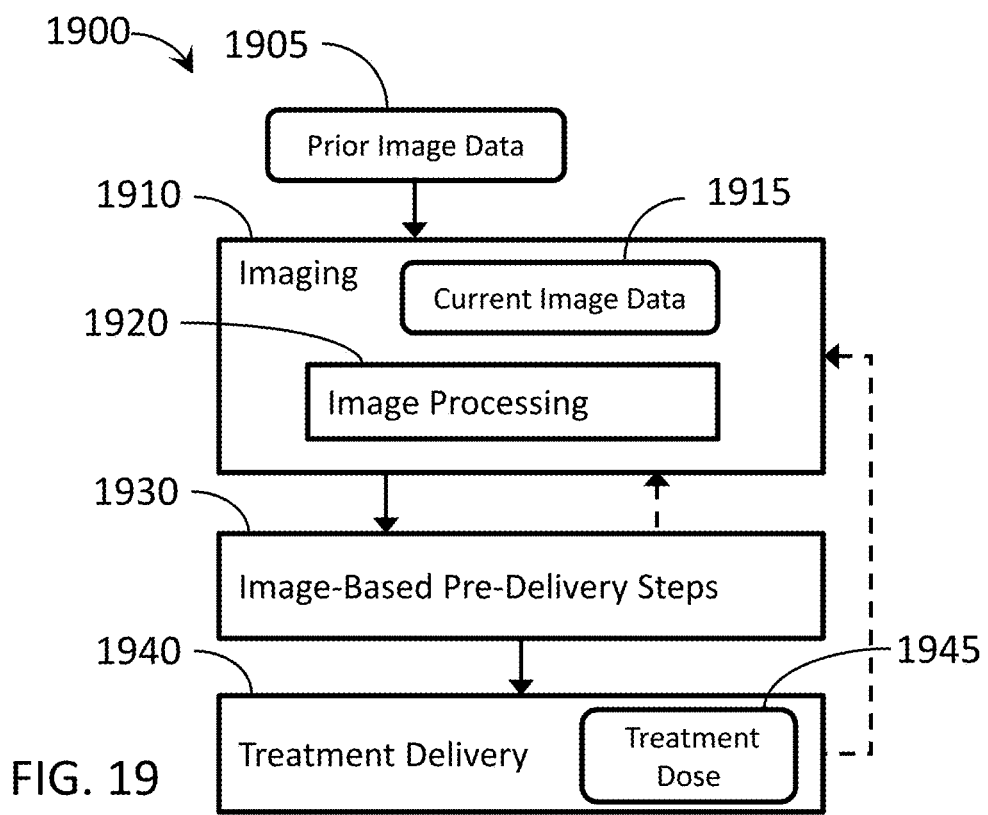
FIG. 19 is a flow chart depicting an exemplary method of IGRT using a radiotherapy device.

FIG. 19 is a flow chart depicting an exemplary method 1900 of IGRT using a radiotherapy device (including, e.g., imaging apparatus 10). Prior image data 1905 of the patient may be available for use, which may be a previously-acquired planning image, including a prior CT image. Prior data 1905 can also include treatment plans, phantom information, models, a priori information, etc. In some embodiments, prior image data 1905 is generated by the same radiotherapy device, but at an earlier time. At step 1910, imaging of a patient is performed using a source of low-energy radiation (e.g., kV radiation from x-ray source 30). In one embodiment, imaging comprises a helical scan with a fan or cone beam geometry. Step 1910 can produce high-quality (HQ) image(s) or imaging data 1915 using the scatter estimation and correction techniques described above. In some embodiments, image quality may be adjusted to optimize a balance between image quality/resolution and dosage. In other words, not all images need to be of the highest quality or image quality may be adjusted to optimize or trade off a balance between image quality/resolution and image acquisition time. Imaging step 1910 can also include image processing to generate patient images based on the imaging data (e.g., in accordance with the methods described above). Although image processing step 1920 is shown as part of imaging step 1910, in some embodiments image processing step 1920 is a separate step, including where image processing is executed by separate devices.

Next, at step 1930, one or more image-based pre-delivery steps, discussed below, are performed based at least in part on the imaging data 1915 from step 1910. As discussed in more detail below, step 1930 can include determining various parameters associated with the therapeutic treatment and (subsequent) imaging planning. In some embodiments, image-based pre-delivery steps (1930) may require more imaging (1910) before treatment delivery (1940). Step 1930 can include adapting a treatment plan based on the imaging data 1915 as part of an adaptive radiotherapy routine. In some embodiments, image-based pre-delivery steps 1930 may include real-time treatment planning. Embodiments may also include simultaneous, overlapping, and/or alternating activation of the imaging and therapeutic radiation sources. Real-time treatment planning may involve any or all of these types of imaging and therapeutic radiation activation techniques (simultaneous, overlapping, and/or alternating).

Next, at step 1940, therapeutic treatment delivery is performed using a source of high-energy radiation (e.g., MV radiation from therapeutic radiation source 20). Step 1940 delivers a treatment dose 1945 to the patient according to the treatment plan. In some embodiments, the IGRT method 1900 may include returning to step 1910 for additional imaging at various intervals, followed by image-based pre-delivery steps (1930) and/or treatment delivery (1940) as required. In this manner the high-quality imaging data 1915 may be produced and utilized during IGRT using one apparatus 10 that is capable of adaptive therapy. As mentioned above, steps 1910, 1920, 1930, and/or 1940 may be executed simultaneously, overlapping, and/or alternating.

IGRT can include at least two general goals: (i) to deliver a highly conformal dose distribution to the target volume; and (ii) to deliver treatment beams with high accuracy throughout every treatment fraction. A third goal can be to accomplish the two general goals in as little time per fraction as possible. Delivering treatment beams accurately requires the ability to identify and/or track the location of the target volume intrafraction with high-quality images. The ability to increase delivery speed requires the ability to accurately, precisely, and quickly move the radiation source according to the treatment plan.

Figure 20:
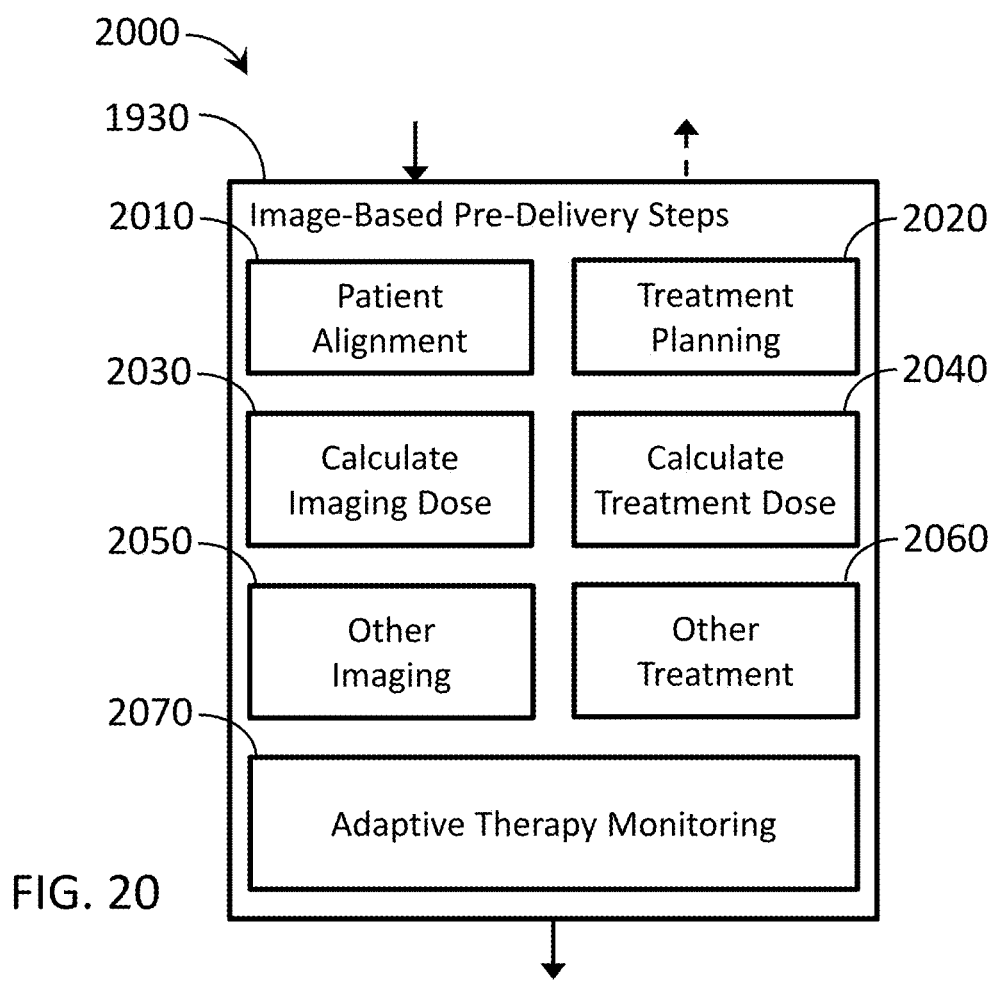
FIG. 20 is a block diagram depicting exemplary image-based pre-delivery steps.

FIG. 20 is a block diagram 2000 depicting exemplary image-based pre-delivery steps/options that may be associated with step 1930 above. It will be appreciated that the above-described imaging apparatus 10 (e.g., as part of a radiotherapy device) can generate kV images that can be used in a variety of ways, including for image-based pre-delivery steps (1930), without departing from the scope of the present invention. For example, images 1915 generated by the radiotherapy device can be used to align a patient prior to treatment (2010). Patient alignment can include correlating or registering the current imaging data 1915 with imaging data associated with earlier pre-treatment scans and/or plans, including the treatment plan. Patient alignment can also include feedback on the physical position of the patient relative to the radiation source to verify whether the patient is physically within the range of the delivery system. If necessary, the patient can be adjusted accordingly. In some embodiments, patient alignment imaging may purposely be of lesser quality to minimize dosage but provide adequate alignment information.

Images generated by the imaging apparatus 10 can also be used for treatment planning or re-planning (2020). In various embodiments, step 2020 can include confirming the treatment plan, modifying the treatment plan, generating a new treatment plan, and/or choosing a treatment plan from a set of treatment plans (sometimes referred to as "plan of the day"). For example, if the imaging data 1915 shows that the target volume or ROI is the same as when the treatment plan was developed, then the treatment plan can be confirmed. However, if the target volume or ROI is not the same, re-planning of the therapeutic treatment may be necessary. In the case of re-planning, because of the high quality of the imaging data 1915 (generated by the x-ray imaging apparatus 10 at step 1910), the imaging data 1915 may be used for treatment planning or re-planning (e.g., generating a new or modified treatment plan). In this manner, pre-treatment CT imaging via a different device is not necessary. In some embodiments, confirming and/or re-planning may be an ongoing procedure before and/or after various treatments.

In accordance with another exemplary use case, images generated by the imaging apparatus 10 can be used to calculate imaging dose (2030), which may be used for ongoing determinations of total dose to the patient and/or for subsequent imaging planning. The quality of subsequent imaging may also be determined as part of the treatment planning, for example, to balance quality and dosage. In accordance with another exemplary use case, images generated by the imaging apparatus 10 can be used to calculate treatment dose (2040), which may be used for ongoing determinations of total dose to the patient and/or may be included as part of treatment planning or re-planning.

In accordance with other exemplary use cases, images generated by the imaging apparatus 10 can be used in connection with planning or adjusting other imaging (2050) and/or other treatment (2060) parameters or plans, including, for example, as part of adaptive therapy and/or treatment plan generation. In accordance with another exemplary use case, images generated by the imaging apparatus 10 can be used in connection with adaptive therapy monitoring (2070), which can include monitoring treatment delivery and adapting as required.

It should be appreciated that the image-based pre-delivery steps (1930) are not mutually exclusive. For example, in various embodiments, calculate treatment dose (2040) can be a step by itself and/or can be part of adaptive therapy monitoring (2070) and/or treatment planning (2020). In various embodiments, the image-based pre-delivery steps (1930) can be performed automatically and/or manually with human involvement.

The devices and methods described above, including the adjustable collimation of the image radiation and the scatter estimation and correction schemes, provide improved scatter estimation, which results in kV-generated images of higher quality than conventional in-treatment imaging systems like CBCT.

Figure 21:
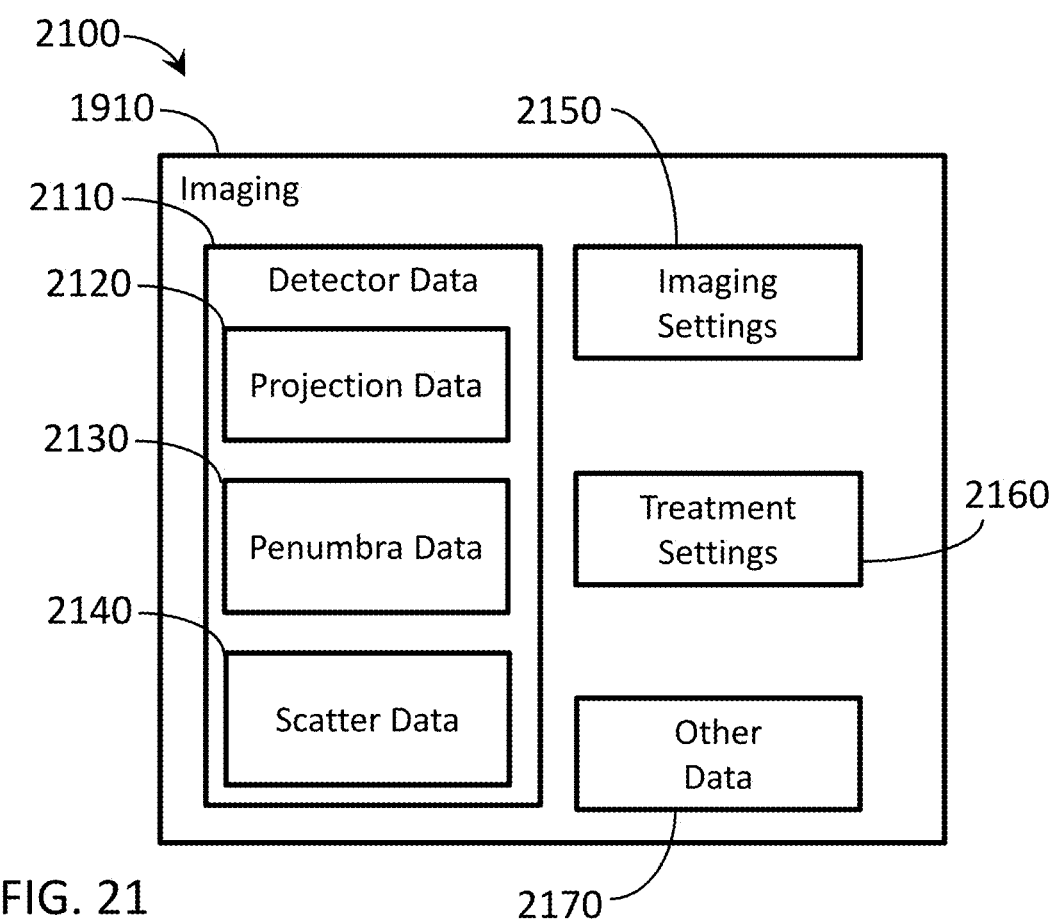
FIG. 21 is a block diagram depicting exemplary data sources that may be utilized during imaging or image-based pre-delivery steps.

FIG. 21 is a block diagram 2100 depicting exemplary data sources that may be utilized during imaging (1910) and/or subsequent image-based pre-delivery steps (1930). Detector data 2110 represents all of the data received by the image radiation detector 34. The projection data 2120 is the data generated by the radiation incident in the collimated beam area, referred to above as the primary or central region. The penumbra data 2130 is the data generated by the radiation incident in the penumbra area. The scatter data 2140 is the data generated by the radiation incident in the peripheral area outside of the penumbra area, referred to above as the shadow region(s).

In one embodiment, the penumbra data 2130 may be used to separate or identify the projection and/or scatter data. As described in detail above, the scatter data 2140 can be used to estimate the scatter radiation in the projection data 2120. In another embodiment, the scatter data 2140 can be used to determine the residual effect of the scatter from the therapeutic radiation source 20 (e.g., MV) when the two sources 20, 30 are operated simultaneously or in an interleaved manner.

In this manner, the penumbra data 2130 and/or the scatter data 2140 may be utilized to improve the quality of the images generated by the imaging step 1910. In some embodiments, the penumbra data 2130 and/or the scatter data 2140 may be combined with the projection data 2120 and/or analyzed in view of the applicable imaging settings 2150, treatment settings 2160 (e.g., if simultaneous imaging and treatment radiation), and any other data 2170 associated with the imaging apparatus 10 at the time of the data collection at the imaging detector 34. In other embodiments, the data may be used for the treatment planning step 1930.

Although the disclosed technology has been shown and described with respect to a certain aspect, embodiment or embodiments, it is obvious that equivalent alterations and modifications will occur to others skilled in the art upon the reading and understanding of this specification and the annexed drawings. In particular regard to the various functions performed by the above described elements (components, assemblies, devices, members, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary aspect, embodiment or embodiments of the disclosed technology. In addition, while a particular feature of the disclosed technology may have been described above with respect to only one or more of several illustrated aspects or embodiments, such feature may be combined with one or more other features of the other embodiments, as may be desired and advantageous for any given or particular application.

While the embodiments discussed herein have been related to the systems and methods discussed above, these embodiments are intended to be exemplary and are not intended to limit the applicability of these embodiments to only those discussions set forth herein. While the present invention has been illustrated by the description of embodiments thereof, and while the embodiments have been described in some detail, it is not the intention of the applicant to restrict or in any way limit the scope of the appended claims to such detail. Additional advantages and modifications will readily appear to those skilled in the art. Therefore, the invention in its broader aspects is not limited to the specific details, representative apparatus and methods, and illustrative examples shown and described. Accordingly, departures may be made from such details without departing from the spirit or scope of the applicant's general inventive concept.

The invention claimed is:

1. A method of estimating scatter in x-ray images, comprising:
   receiving measured projection data from a primary region of an x-ray detector, wherein the primary region of the x-ray detector is directly exposed to a radiation beam from a radiation source during at least one scan;
   receiving measured scatter data from at least one shadow region of the x-ray detector, wherein the at least one shadow region of the x-ray detector is blocked from direct exposure to the radiation beam; and
   determining an estimated scatter in the measured projection data based on the measured scatter data in the at least one shadow region;
   wherein an aperture center of the primary region is offset from a readout center of the readout range during the at least one scan.

2. The method of claim 1, further comprising:
   adjusting a position of the radiation beam such that the aperture center of the primary region is offset from the readout center of the x-ray detector.

3. The method of claim 1, wherein the at least one scan comprises a first scan and a second scan, and wherein the at least one shadow region comprises a first shadow region and a second shadow region, the method further comprising:
   adjusting a position of the radiation beam between the first scan and the second scan, such that the first shadow region overlaps with a first side of the readout range during the first scan and the second shadow region overlaps with a second side of the readout range during the second scan;
   wherein determining the estimated scatter in the measured projection data is based on the measured scatter data in the first shadow region and the second shadow region.

4. The method of claim 3, wherein the second side of the readout range aligns with a first penumbra region opposite the first shadow region during the first scan, and wherein the first side of the readout range aligns with a second penumbra region opposite the second shadow region during the second scan.

5. The method of claim 3, wherein the first scan comprises a first radiation dose and the second scan comprises a second radiation dose different than the first radiation dose.

6. The method of claim 5, wherein determining the estimated scatter in the measured projection data comprises scaling the measured scatter data in at least one of the first shadow region or the second shadow region based on a difference between the first radiation dose and the second radiation dose.

7. The method of claim 5, wherein determining the estimated scatter in the measured projection data comprises scaling the measured projection data from at least one of the first scan or the second scan based on a difference between the first radiation dose and the second radiation dose.

8. The method of claim 3, wherein determining the estimated scatter in the measured projection data comprises reconstructing the measured projection data from the first scan and the second scan jointly.

9. The method of claim 1, further comprising:
receiving measured penumbra data in at least one penumbra region; and
determining the estimated scatter in the primary region based on the measured penumbra data in the at least one penumbra region.

10. The method of claim 9, wherein determining the estimated scatter in the primary region based on the measured penumbra data in the at least one penumbra region comprises determining the estimated scatter in primary region pixels adjacent to penumbra region pixels.

11. The method of claim 10, wherein determining the estimated scatter in the primary region based on the measured penumbra data in the at least one penumbra region comprises an iterative process.

12. The method of claim 9, wherein determining the estimated scatter in the primary region comprises weighting the measured scatter data in the at least one shadow region different than the measured penumbra data in the at least one penumbra region.

13. An x-ray imaging apparatus, comprising:
a rotating x-ray source for emitting a radiation beam;
an x-ray detector positioned to receive radiation from the x-ray source, wherein the detector includes a readout range;
a beamformer configured to adjust a shape of the radiation beam emitted by the x-ray source, such that a primary region of the x-ray detector is directly exposed to the radiation beam and at least one shadow region of the x-ray detector is blocked from direct exposure to the radiation beam by the beamformer;
wherein an aperture center of the primary region is offset from a readout center of the readout range; and
a data processing system configured to:
receive measured projection data in the primary region and measured scatter data in the at least one shadow region; and
determine an estimated scatter in the primary region based on the measured scatter data in the at least one shadow region.

14. The x-ray imaging apparatus of claim 13, wherein the data processing system is further configured to:
receive measured penumbra data in at least one penumbra region; and
determine the estimated scatter in the primary region based on the measured penumbra data in the at least one penumbra region.

15. The x-ray imaging apparatus of claim 13, wherein the beamformer adjusts a position of the of the radiation beam such that the aperture center of the primary region is offset from a detector center of the x-ray detector.

16. The x-ray imaging apparatus of claim 13, wherein the readout center of the readout range is offset from a detector center of the x-ray detector.

17. The x-ray imaging apparatus of claim 13, wherein the beamformer adjusts a position of the of the radiation beam such that the aperture center of the primary region is offset from a detector center of the x-ray detector, and wherein the readout center of the readout range is offset from a detector center of the x-ray detector.

18. The x-ray imaging apparatus of claim 13, wherein the at least one shadow region of the x-ray detector comprises a back shadow region with a back axial length and a front shadow region with a front axial length, and wherein the back axial length is not equal to the front axial length.

19. A radiotherapy delivery device comprising:
a rotatable gantry system positioned at least partially around a patient support;
a first source of radiation coupled to the rotatable gantry system, the first source of radiation being configured as a source of therapeutic radiation;
a second source of radiation coupled to the rotatable gantry system, the second source of radiation being configured as a source of imaging radiation having an energy level less than the source of therapeutic radiation;
a radiation detector coupled to the rotatable gantry system and positioned to receive radiation from the second source of radiation;
a beamformer configured to adjust a shape of a radiation beam emitted by the second source of radiation, such that a primary region of the radiation detector is directly exposed to the radiation beam and at least one shadow region of the radiation ray detector is blocked from direct exposure to the radiation beam by the beamformer; and
a data processing system configured to:
receive measured projection data in the primary region and measured scatter data in the at least one shadow region; and
determine an estimated scatter in the primary region based on the measured scatter data in the at least one shadow region, wherein an aperture center of the primary region is offset from a readout center of the readout range;
reconstruct a patient image based on the estimated scatter; and
deliver a dose of therapeutic radiation to the patient via the first radiation source based on the patient image during adaptive IGRT.

* * * * *